United States Patent
Mougin et al.

(10) Patent No.: US 9,757,035 B2
(45) Date of Patent: Sep. 12, 2017

(54) THREE-DIMENSIONAL PLANTAR IMAGING APPARATUS AND MEMBRANE ASSEMBLY FOR USE IN THE SAME

(71) Applicant: CRYOS TECHNOLOGIES INC., Joliette (CA)

(72) Inventors: Patrick Mougin, Joliette (CA); Mohamed Lachhab, Joliette (CA); Philippe Légaré, Joliette (CA)

(73) Assignee: CRYOS TECHNOLOGIES INC, Joliette, Québec (CA)

( * ) Notice: Subject to any disclaimer, the term of this patent is extended or adjusted under 35 U.S.C. 154(b) by 0 days.

(21) Appl. No.: 15/032,273

(22) PCT Filed: May 20, 2015

(86) PCT No.: PCT/CA2015/050453
§ 371 (c)(1),
(2) Date: Apr. 26, 2016

(87) PCT Pub. No.: WO2015/176183
PCT Pub. Date: Nov. 26, 2015

(65) Prior Publication Data

US 2016/0249807 A1     Sep. 1, 2016

Related U.S. Application Data

(60) Provisional application No. 62/001,488, filed on May 21, 2014.

(51) Int. Cl.
*A61B 5/00* (2006.01)
*A61B 5/107* (2006.01)

(52) U.S. Cl.
CPC ............ *A61B 5/004* (2013.01); *A61B 5/0064* (2013.01); *A61B 5/0073* (2013.01);
(Continued)

(58) Field of Classification Search
CPC .................................. A61B 5/00; A61B 5/107
(Continued)

(56) References Cited

U.S. PATENT DOCUMENTS 5,088,503 A     2/1992  Seitz
6,205,230 B1 *  3/2001  Sundman ............. A61B 5/0064
                                               382/100

(Continued)

FOREIGN PATENT DOCUMENTS

| CA | 2730475 A1 | 1/2010 |
| CA | 2888468 A1 | 4/2014 |
| WO | 03087717 A1 | 10/2003 |

OTHER PUBLICATIONS

"Cinderella Ski Boot Fit", WildSnow.com, Lisa Dawson, 2012, https://www.wildsnow.com/8557/cinderella-backcountry-boot-fit/.*

(Continued)

*Primary Examiner* — Tse Chen
*Assistant Examiner* — Joanne Hoffman
(74) *Attorney, Agent, or Firm* — Foley & Lardner LLP; James De Vellis

(57) ABSTRACT

A membrane assembly for use with a three-dimensional imager to obtain a topographical plantar image of a foot is provided. The assembly includes a support structure having a front end and a rear end elevated relative to the front end, and a flexible membrane suspended from the support structure and configured to receive and support an entire plantar surface of the foot. The membrane defines and encloses an upper portion of an inflatable chamber, and includes a forefoot- and a rearfoot-receiving region respectively adjacent to the front and the rear end of the support structure. The rearfoot-receiving region is under less tension than the forefoot-receiving region. The imager is positionable under the membrane in order to acquire the plantar image when the (Continued)

foot is disposed on the membrane. An apparatus including a membrane assembly and a three-dimensional imager, and a method for imaging a foot are also provided.

28 Claims, 19 Drawing Sheets

(52) U.S. Cl.
CPC .......... *A61B 5/1074* (2013.01); *A61B 5/1079* (2013.01); *A61B 5/1077* (2013.01)

(58) Field of Classification Search
USPC .......................................................... 600/476
See application file for complete search history.

(56) References Cited

U.S. PATENT DOCUMENTS

| 7,552,494 | B2* | 6/2009 | Peterson | ................. | A43D 1/02 |
| | | | | | 12/1 R |
| 2006/0076700 | A1* | 4/2006 | Phillips | ................... | A43B 7/28 |
| | | | | | 264/40.1 |
| 2006/0103852 | A1 | 5/2006 | Klaveness | | |
| 2006/0283243 | A1 | 12/2006 | Peterson | | |
| 2011/0313321 | A1 | 12/2011 | Alfaro Santafe et al. | | |
| 2014/0276094 | A1* | 9/2014 | Lidtke | ................. | A61B 5/1079 |
| | | | | | 600/476 |

OTHER PUBLICATIONS

International Preliminary Report on Patentability for International PCT Application No. PCT/CA2015/050453, dated Jul. 27, 2015.
Written Opinion of International Searching Authority and International Search Report for International Application No. PCT/CA2015/050453, dated Jul. 27, 2015.

* cited by examiner

THREE-DIMENSIONAL PLANTAR IMAGING APPARATUS AND MEMBRANE ASSEMBLY FOR USE IN THE SAME

CROSS-REFERENCE TO A RELATED APPLICATION

This application claims priority under 35 U.S.C. §119(e) of U.S. provisional patent application No. 62/001,488 filed on May 21, 2014, the specification of which is hereby incorporated by reference in its entirety.

TECHNICAL FIELD

The general technical field relates to techniques for acquiring the plantar foot shape of a patient for manufacturing a patient-specific orthosis and, in particular, to techniques for acquiring a three-dimensional image of the plantar surface of a foot.

BACKGROUND

Various techniques exist for measuring the three-dimensional (3D) shape of a foot for the production of orthoses. The traditional technique generally involves forming a cast and mold of the foot in a non-weight-bearing condition. Despite having certain advantages in terms of simplicity and cost, the casting techniques can be relatively time consuming and labor intensive, which limit the number of patients that a practitioner can treat daily.

More recent techniques have relied on optical imaging techniques to acquire a 3D plantar foot shape, typically using a digital laser scanner. The image data can subsequently be used in a computer-aided design and manufacturing (CAD/CAM) system to fabricate a patient-specific orthosis. Optical imaging techniques can provide time and cost advantages over traditional casting and molding techniques and, depending on the intended application, can allow the 3D plantar image to be acquired in any of a non-weight-bearing, full-weight-bearing and semi-weight-bearing state, each having its own challenges and limitations.

For example, measurement techniques that acquire an image of the plantar surface with the foot in a non-weight-bearing state generally cannot account for the natural elongation and deformation of the foot that occur when weight is applied thereto, which can lead to unreliable measurements. Meanwhile, in a full-weight-bearing condition, the deformation imposed on the foot can become significant enough so as to negatively affect the reliability of the scanned image, notably the arch measurements. It can also be difficult to position the foot in a neutral position in a full-weight-bearing condition. A semi-weight-bearing condition can provide an intermediate and, in principle, more accurate configuration to acquire an image of the plantar surface, as this condition is often more representative of the natural elongation and deformation of the foot in the walking stance. However, acquiring a 3D plantar image with the entire length of the foot in a semi-weight-bearing state is not straightforward, as achieving proper soft tissue deformation requires careful positioning of the foot, which can prove challenging using existing techniques.

Accordingly, many challenges remain in the development of techniques for acquiring a 3D plantar image with the whole foot in a semi-weight-bearing condition, while also overcoming or at least alleviating some of the drawbacks of existing techniques.

SUMMARY

In accordance with an aspect, there is provided a membrane assembly for use with a three-dimensional imager to obtain a topographical plantar image of a foot. The membrane assembly includes:
  a support structure having a front end and a rear end, the rear end being elevated relative to the front end; and
  a flexible membrane suspended from the support structure and configured to receive and support an entire plantar surface of the foot, the flexible membrane defining and enclosing an upper portion of an inflatable chamber, the flexible membrane including a forefoot-receiving region and a rearfoot-receiving region respectively adjacent to the front end and the rear end of the support structure, the rearfoot-receiving region being under less tension than the forefoot-receiving region, the three-dimensional imager being positionable under the flexible membrane in order to acquire the topographical plantar image when the foot is disposed on the flexible membrane.

In accordance with another aspect, there is provided an apparatus for obtaining a topographical plantar image of a foot in a semi-weight-bearing condition. The apparatus includes:
  a three-dimensional imager;
  a support structure having a front end and a rear end, the rear end being elevated relative to the front end; and
  a flexible membrane suspended from the support structure and configured to receive an entire plantar surface of the foot thereon, the flexible membrane defining and enclosing an upper portion of an inflatable chamber, the flexible membrane including a forefoot-receiving region and a rearfoot-receiving region respectively adjacent to the front end and the rear end of the support structure, the rearfoot-receiving region being under less tension than the forefoot-receiving region, the three-dimensional imager being provided under the flexible membrane in order to acquire the topographical plantar image when the foot is disposed on the flexible membrane.

In accordance with a further aspect, there is provided a method for imaging a foot having a front portion and a rear portion. The method includes:
  providing a flexible membrane suspended from a support structure having a front end and a rear end elevated relative to the front end, the flexible membrane defining and enclosing an upper portion of an inflatable chamber, the flexible membrane including a forefoot-receiving region and a rearfoot-receiving region respectively affixed to the front end and the rear end of the support structure, the rearfoot-receiving region being under less tension than the forefoot-receiving region;
  adjusting an internal pressure of the inflatable chamber;
  positioning the foot on the membrane in a semi-weight-bearing condition with an entire plantar surface of the foot being supported by the flexible membrane with the front and rear portions of the foot respectively located in the forefoot and rearfoot-receiving regions of the membrane; and
  acquiring a topographical plantar image of the foot.

In some implementations, the providing step includes preforming the flexible membrane so that the flexible membrane has a concave recessed area in the rearfoot-receiving region.

In some implementations, the providing step includes mounting the flexible membrane to the support structure so that the flexible membrane has a concave recessed area in the rearfoot-receiving region.

In some implementations, the providing step includes securing the flexible membrane to the support structure.

In some implementations, the method further includes, between the positioning step and the acquiring step, a step of readjusting the internal pressure of the inflatable chamber.

In some implementations, the method further includes between the providing step and the adjusting step, a step of applying a compressive load on the flexible membrane along a peripheral portion of the forefoot-receiving region.

In accordance with another aspect, there is provided a use of the membrane assembly as described herein, in conjunction with a three-dimensional imager, for obtaining a topographical plantar image of a foot.

In accordance with another aspect, there is provided a use of the apparatus as described herein for obtaining a topographical plantar image of a foot.

Other features and advantages of aspects of the present invention will be better understood upon reading of preferred embodiments thereof with reference to the appended drawings.

DETAILED DESCRIPTION

Figure 1:
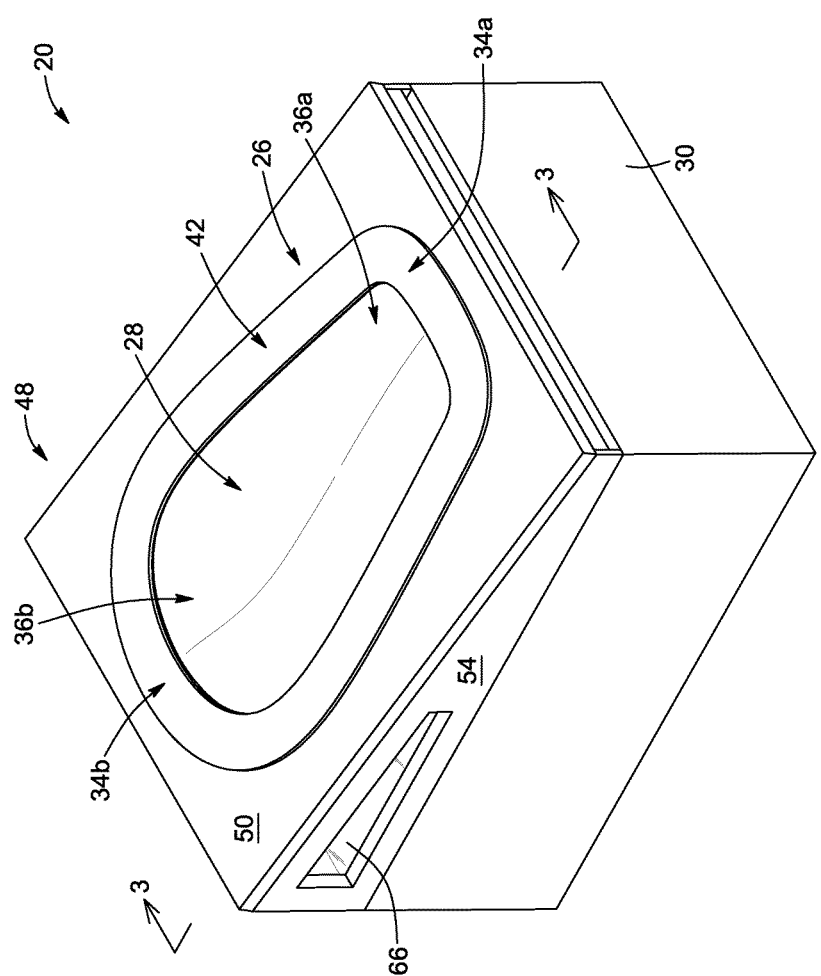
FIG. 1 is schematic perspective view of an apparatus for obtaining a topographical image of a plantar surface of a foot, in accordance with an embodiment.

In the following description, similar features in the drawings have been given similar reference numerals, and, in order to not unduly encumber the figures, some elements may not be indicated on some figures if they were already identified in preceding figures. It should also be understood herein that the elements of the drawings are not necessarily depicted to scale, since emphasis is placed upon clearly illustrating the elements and structures of the present embodiments.

The present description generally relates to techniques for obtaining a topographical plantar image of a foot. In particular, in accordance with different aspects, there are provided a membrane assembly for use with a 3D imager, an apparatus including a membrane assembly and a 3D imager, and a method for imaging the plantar surface of a foot.

As used herein, the term "topographical plantar image" and variants thereof broadly refer to a 3D relief map or model replicating the plantar foot surface in a certain weight-bearing condition. The topographical plantar image generally consists of arrays of 3D data points, each described by its spatial coordinate $Z(x, y)$, where Z is the local height or elevation of the surface at position $(x, y)$. As described below, a topographical image of the plantar shape can be acquired using optical methods, for example 3D laser scanners, and 3D digital stereo imaging systems.

As used herein, the term "plantar surface" has its ordinary meaning and refers to the underside or bottom surface of the foot.

As known in the art, topographical plantar images may be acquired with the foot in three main weight-bearing conditions: non-weight bearing, full-weight bearing and semi-weight bearing. First, the term "non-weight bearing" refers to a weight-bearing condition where no body weight or forces are applied to the foot, as if the foot were in suspension. Meanwhile, the term "full-weight bearing" refers to a weight-bearing condition where the foot supports the whole body weight. Finally, the term "semi-weight bearing" refers to a weight-bearing condition where only a certain amount of body weight is applied supported by the foot, such as, for example, between 20% and 50% of the total body weight. Of course, this range is provided for exemplary purposes only, such that values lying outside this range can be used in certain embodiments. It is to be noted that, in the present description, the terms "semi-weight bearing" and "partial-weight bearing" can be used interchangeably.

As mentioned above, in some instances, acquiring a 3D plantar image with the foot in a semi-weight-bearing state may be desirable. One reason for this is that the amount of soft tissue deformation under semi-weight bearing can be controlled more accurately and be more representative of the natural physiological deformation of the foot under body weight, for example the height of the medial and lateral arches and the natural deformation of the foot axis. Hence, measuring the 3D plantar shape under some controlled level of deformation can be beneficial, while an absence or excess of deformation, as in non-weight-bearing and full-weight-bearing conditions, can lead to inaccuracies in the measured data. Acquiring a 3D plantar image in a semi-weight-bearing condition can be challenging and can involve providing: (i) a foot-receiving surface which is not locally deformed by another physical part of the system (e.g., a plate-like surface) when the foot is received thereon; (ii) a controlled pressure exerted on the foot which is adapted to the flexibility and dimensions of the foot, and which induces a deformation of the foot that is anatomically similar to the natural physiological deformation of the foot under body weight; and (iii) a configuration that can remain stable over the entire duration of the image acquisition process.

The techniques described herein allow for a 3D plantar image to be acquired under semi-weight bearing with the entire plantar surface of the foot received on and supported solely by a flexible and inflatable membrane suspended from a support structure. As will be described in greater detail below, achieving this semi-weight-bearing configuration involves configuring, among other things, the flexible membrane such that the region of the membrane for receiving the rear of the foot (e.g., the heel) is connected higher on the support structure and under less tension than the region of the membrane intended for receiving the front of the foot (e.g., the toes).

Apparatus for Acquiring a 3D Plantar Image and Membrane Assembly

Referring to FIGS. 1 to 7, there is illustrated an exemplary embodiment of an apparatus 20 configured for obtaining a topographical image of a plantar surface 22 of a foot 24. Broadly described, the apparatus 20 generally includes a support structure 26, a flexible membrane 28 suspended from the support structure 26 and configured to receive and support at least partially a weight of the foot 24 thereon, and a 3D imager 30 provided under the flexible membrane 28 to acquire the topographical image of the plantar surface 22 of the foot 24 when the foot 24 is placed on the flexible membrane 28 (see FIGS. 2, 4 and 7). Furthermore, the flexible membrane 28 defines and encloses an upper portion of an inflatable chamber 32. More details regarding the various operational and structural features of the apparatus will be discussed further below.

As used herein, the term "support structure" refers broadly to any structure that can hold and mechanically support the flexible membrane, generally via its periphery, in a manner such that the flexible membrane hangs from the support structure while hermetically sealing the inflatable chamber.

As used herein, the term "flexible membrane" is intended to refer to any sheet-like or otherwise relatively thin layer of elastic and stretchable material which is mechanically deformed in response to the action of an applied load, for example, the force exerted by the weight of the foot received on the membrane. It is noted that for simplicity, the term "flexible membrane" may, in some instances, be shortened to "membrane". In an embodiment, the membrane may have an ultimate elongation greater than 300%, for example 600%, although different values of ultimate elongation may be used in other embodiments. As known in the art, the term "ultimate elongation" refers to the percentage increase in the length of a material that occurs before the mechanical properties of the material change irreversibly (e.g., due to breakage under tension or to the onset of crystallization). It is to be noted that, for the purpose of the present description and unless stated otherwise, the terms "flexible", "elastic", "stretchable", "foldable" and variants thereof can be used interchangeably to designate the ability of the membrane to be deformed under an applied load.

Referring still to FIGS. 1 to 7, the flexible membrane 28 may be made of any suitable flexible material including, without limitation, polymers, plastics, thermoplastics, rubber, synthetic rubbers, elastomers, and the like. For example, in an embodiment, the flexible membrane 28 is made of a silicone-based flexible material. The flexible membrane 28 can be made by casting, molding, extrusion, thermoforming, 3D printing, or any other suitable manufacturing process or technique. The flexible membrane 28 may have a thickness ranging from about 0.5 millimeter (mm) to about 4 mm, and particularly between about 0.8 mm and about 1.2 mm. For example, in the illustrated embodiment, the thickness of the membrane 28 is 0.8 mm. It is to be noted that the flexible membrane 28 may, but need not, have a uniform thickness. Also, the membrane 28 may be flat or have a preformed shape (e.g., concave or convex), or have a different configuration on each side thereof. More details regarding the shape and configuration of the flexible membrane will be discussed further below.

The support structure 26 includes a front end 34a and a rear end 34b, which are provided such that rear end 34b is elevated relative to front end 34a. As used herein, the term "elevated" refers to the rear end of the support structure being vertically higher than the front end when measured upwardly from the bottom of the apparatus. In an embodiment, the elevation angle of the rear end 34b of the support structure 26 relative to the front end 34a thereof ranges between about 5 degrees and about 30 degrees, and in another embodiment between about 5 degrees and about 6 degrees, although other elevation angle values may be used in other embodiments. It will be understood that, when referring to the relative position of the front and rear ends 34a, 34b of the support structure 26, the term "elevation angle" of the support structure 26 is defined as the tangent of the elevation angle which is equal to the ratio of the vertical distance to the horizontal distance between the front end 34a and the read end 34b.

The flexible membrane 28 includes a forefoot-receiving region 36a and a rearfoot-receiving region 36b proximate and affixed to the front end 34a and the rear end 34b of the support structure 26, respectively. It is understood that, when designating the regions of the flexible membrane 28, the terms "forefoot" and "rearfoot" refer to the fact that the forefoot and the rearfoot-receiving regions 36a, 36b are intended to receive and support the front and rear portions 38a, 38b of the foot 24, respectively. As a result of the rear end 34b of the support structure 26 being elevated relative to the front end 34a, the flexible membrane 28 is downwardly inclined toward the forefoot-receiving region 36a. In particular, the inclination angle of the suspended membrane 28 corresponds to the elevation angle of the support structure 26 thereof. In an embodiment, the configuration of the support structure 26 may optionally allow for the elevation angle of the support structure 26, and thus for the inclination angle of the membrane 28, to be adjusted over a certain angular range. More details regarding the advantages of suspending the membrane 28 in a downwardly inclined manner toward the forefoot-receiving region 36a will be discussed further below.

Referring still to FIGS. 1 to 7, the support structure 26 can form part of a housing 48, which generally defines the overall shape of at least an upper portion of the apparatus 20. The housing 48 has a top wall 50, a bottom wall 52, and a sidewall 54 interconnecting the top and bottom walls 50, 52. The sidewall 54 includes four wall panels, but this number may differ in other embodiments. In the illustrated embodiment, one or more transparent windows 66 may optionally be provided on the sidewall 54 to allow for the podiatric physician to better see the foot received on the flexible membrane 28 and more conveniently adjust its position as well as to allow for a camera (not shown) to acquire an image of the membrane 28 when the foot 24 is received thereon. The transparent windows 66 may also be provided to reduce the weight of the apparatus 20. In another embodiment, transparent windows may be omitted and an optional positioning system (not shown) may be provided inside the housing 48 to facilitate the positioning of the foot 24 on the flexible membrane 28. The housing 48 may be made of light yet sturdy and durable material including, without being limited to, molded plastic or lightweight metals alloys. The housing 48 may also be compact and have an ergonomic shape (e.g., rounded corners and smooth surfaces) to facilitate its use and operation.

In the illustrated embodiment, the top wall 50 is inclined at a slope angle θ, which corresponds to the elevation angle of the support structure 26 and, thus, to the inclination angle of the flexible membrane 28. Accordingly, the slope angle θ of the top wall 50 relative to the bottom wall 52 may range between about 5 degrees and about 30 degrees, although other slope angle values may be used in other embodiments. It is also to be noted that, in other embodiments, the angle, if any, between the top and the bottom wall 50, 52 of the housing 48 need not be equal to the elevation angle of the support structure 26.

In the illustrated embodiment, the support structure 26 includes a peripheral frame 42 that encloses an opening 40 formed through the top wall 50 of the housing 48. The flexible membrane 28 is affixed to the peripheral frame 42 in a way such as to extend across and hermetically seal the opening 40. As a result of the opening 40 being hermetically sealed, the flexible membrane 28 and the housing 48 together define and enclose the inflatable chamber 32. In this regard, it will be understood that, in some embodiments, the support structure 26 need not form part of a housing, as long as the flexible membrane 28 is suspended from the support structure 26 and defines and encloses an upper portion of the inflatable chamber 32.

Figure 10:
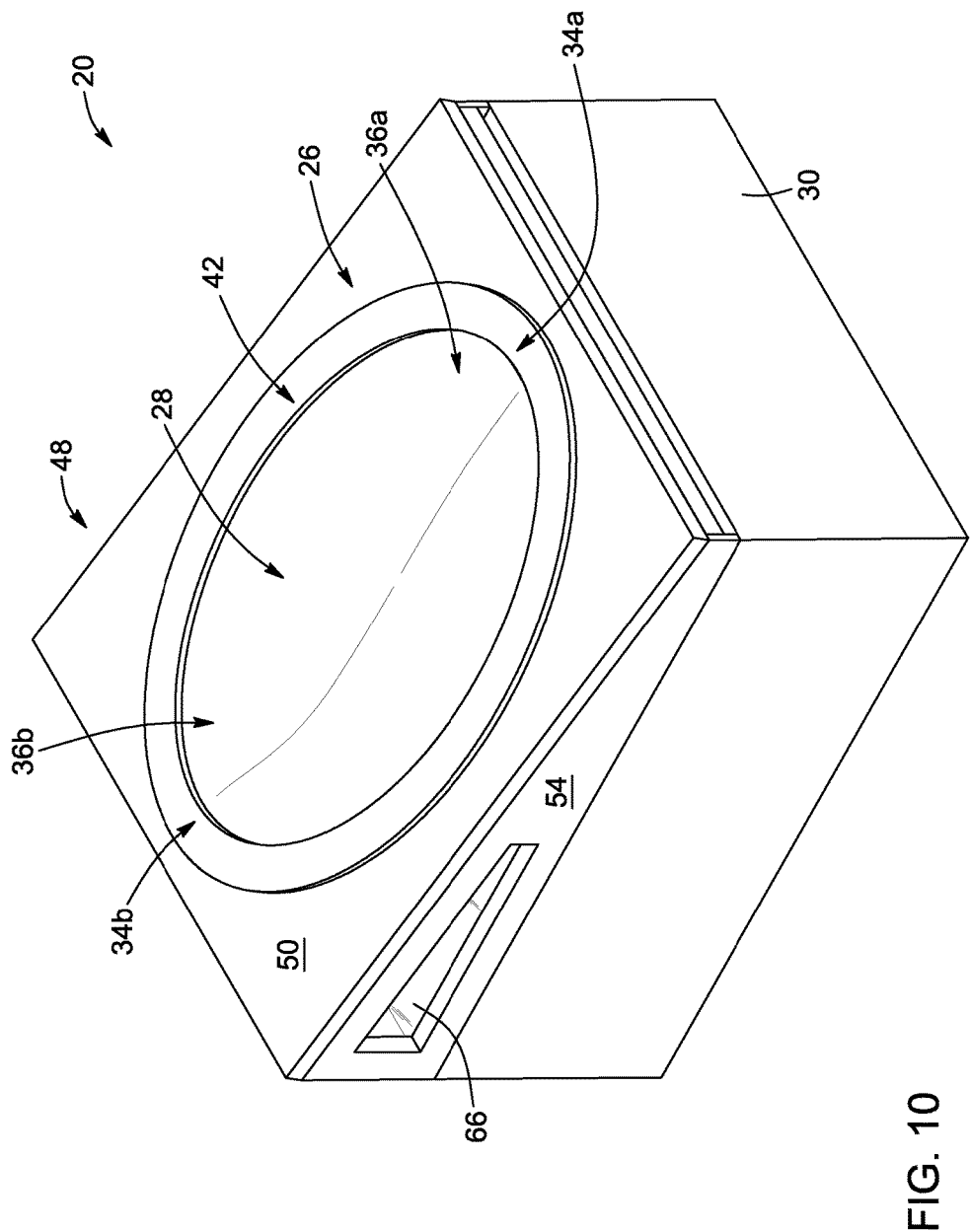
FIG. 10 is a schematic perspective view of an apparatus for obtaining a topographical image of a plantar surface of a foot, in accordance with a further embodiment.
Figure 11:
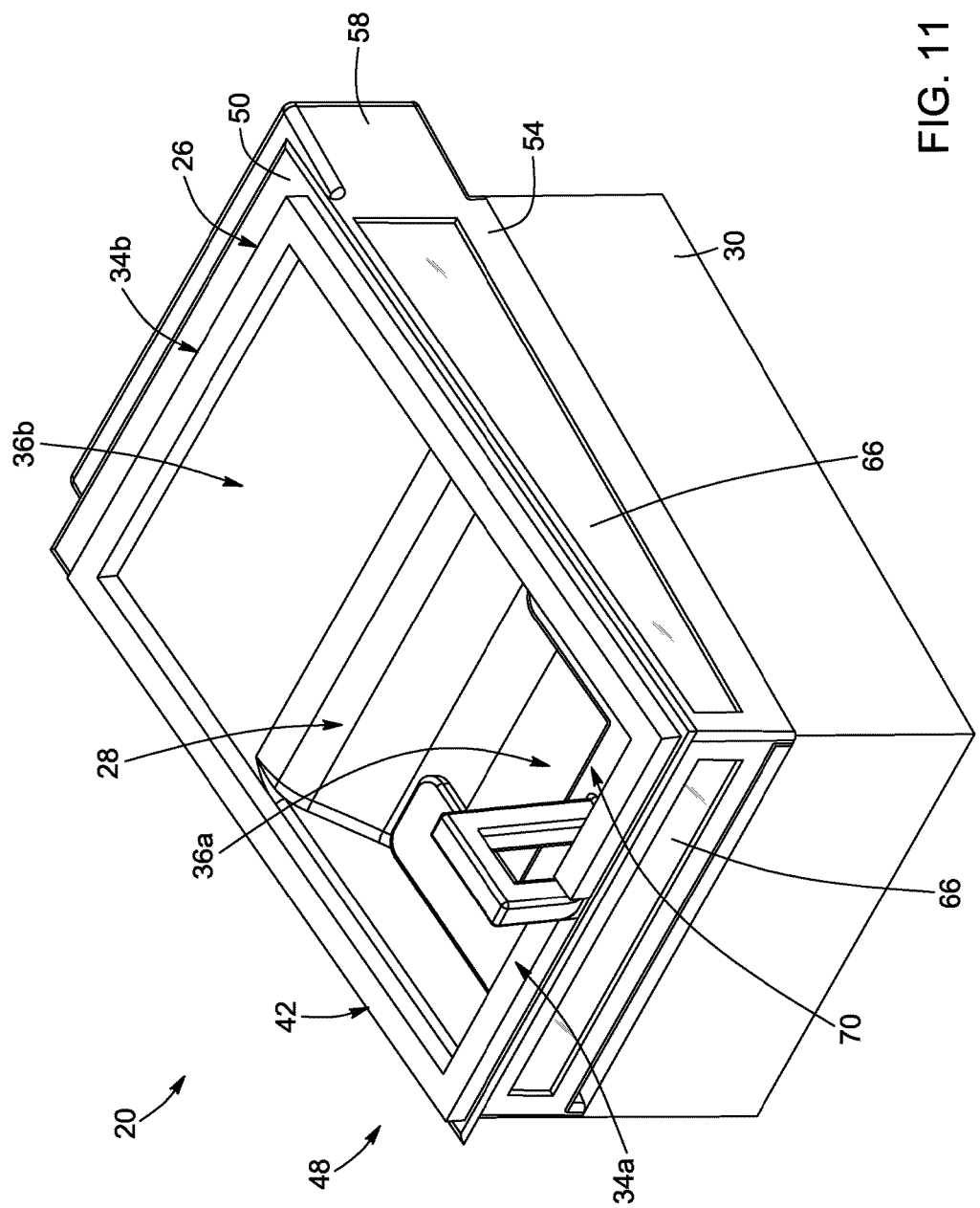
FIG. 11 is a schematic perspective view of an apparatus for obtaining a topographical image of a plantar surface of a foot, in accordance with a still another embodiment.

In the illustrated embodiment, the opening 40 generally has an ovoid shape, with a width that increases from the front end 34a toward the rear end 34b of the support structure 26. Of course, in other embodiments, the opening 40 may have another shape, for example an ellipse (see FIG. 10) or a rectangle (see FIG. 11), or any other suitable regular or irregular shape. Moreover, in other embodiments, the opening 40 may have a substantially uniform width, as depicted in FIGS. 10 and 11. It is to be noted that the term "width" and variants thereof refer herein to a linear dimension that extends perpendicularly to a line extending between the front and the rear ends of the support structure or, equivalently, perpendicularly to the longitudinal axis of the foot when received on the flexible membrane (see, e.g., FIG. 7). More details regarding the advantages of varying the width of the opening enclosed by the peripheral frame of the support structure will be discussed further below.

Figure 3:
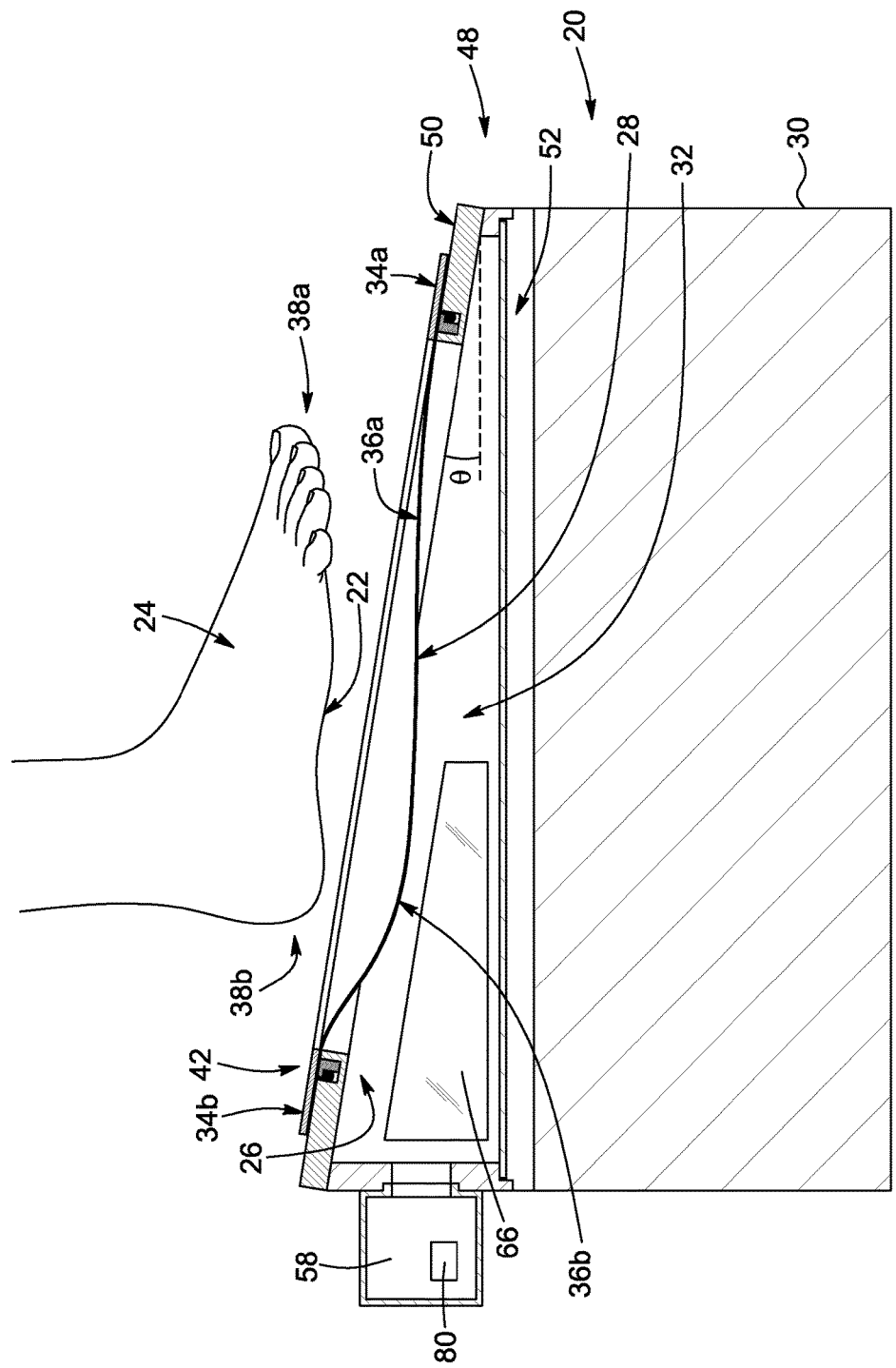
FIG. 3 is a cross-sectional side view of the apparatus of FIG. 1, taken along section line 3 and depicting a foot above the flexible membrane.
Figure 4:
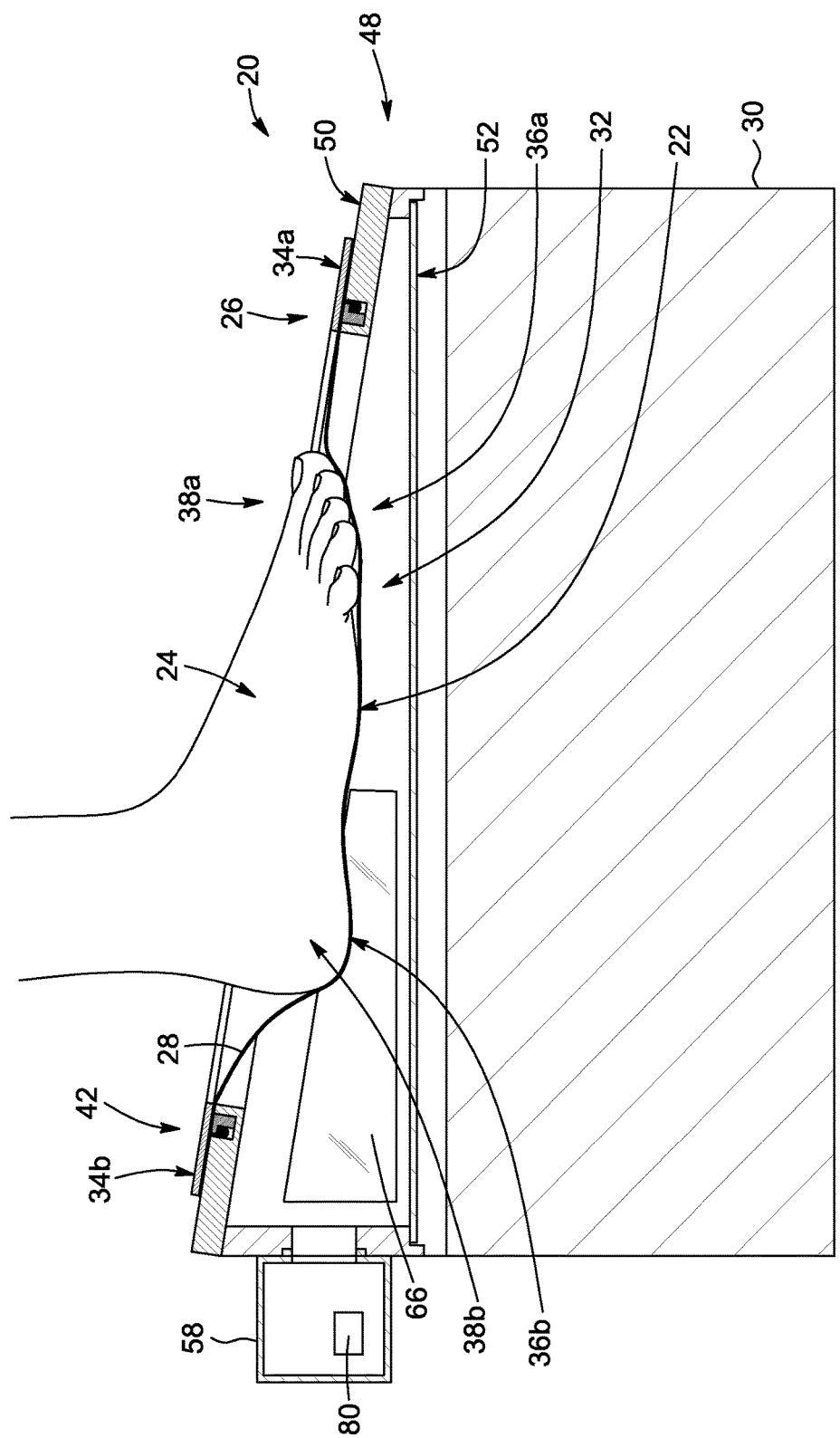
FIG. 4 is the same as FIG. 3, but with the foot received on the flexible membrane.
Figure 5:
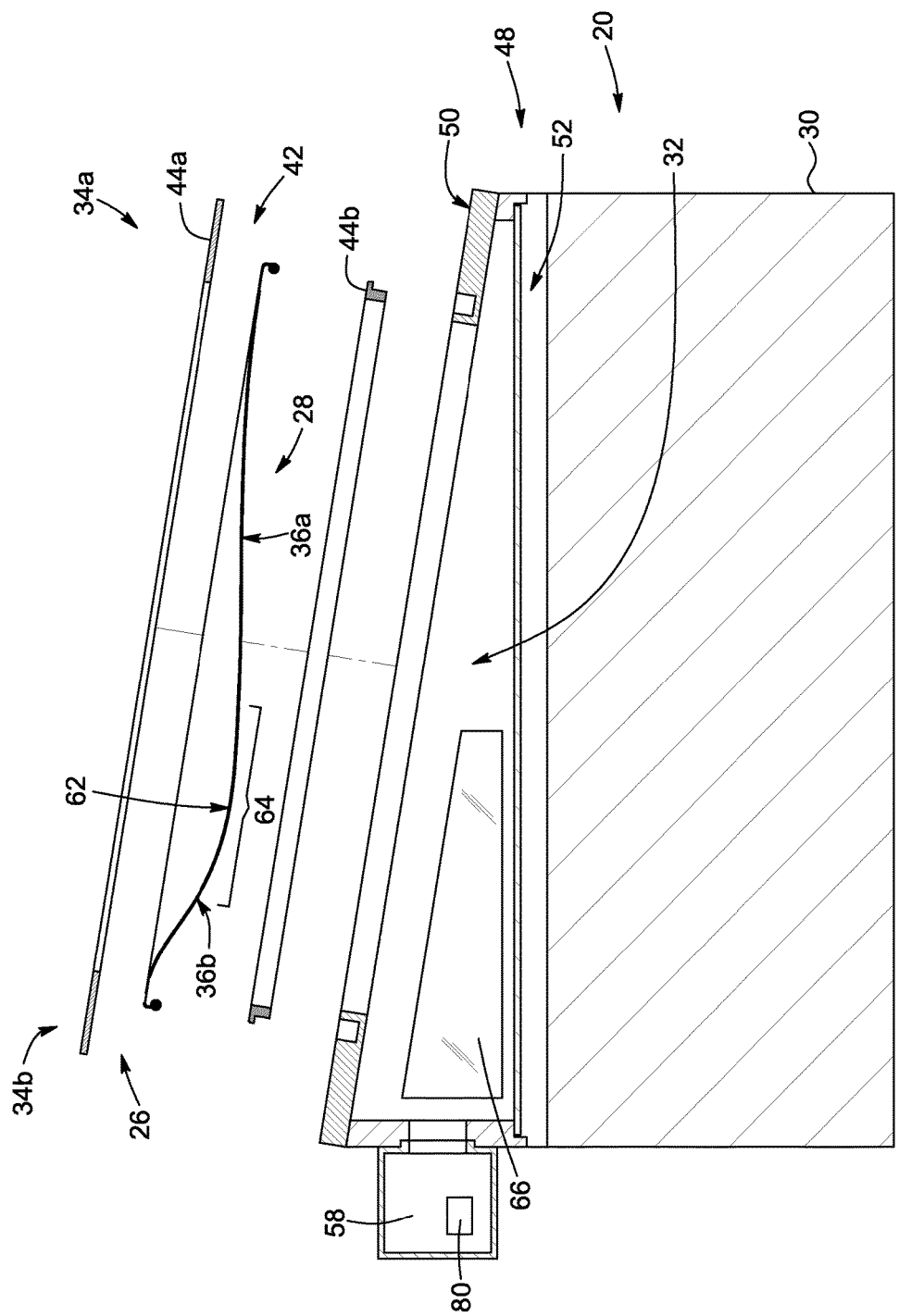
FIG. 5 is a partially exploded, cross-sectional side view of the apparatus of FIG. 1, taken along section line 3-3 and depicting in more detail the configuration of the support structure from which is suspended the flexible membrane.

Turning now to FIGS. 3 to 5, in the illustrated embodiment, the peripheral frame 42 of the support structure 26 includes an upper frame member 44a and a lower frame member 44b, the lower frame member 44b being received in a peripheral groove 46 formed in the top wall 50 of the housing 48. As illustrated in FIGS. 3 to 5, the upper and lower frame members 44a, 44b cooperate to sealingly clamp the periphery of the flexible membrane 28 therebetween and against the outer wall of the peripheral groove 46. In one embodiment, either or both of the upper and lower frame members 44a, 44b are detachably connected to the top wall 50 of the housing 48.

Of course, those skilled in the art will appreciate that the flexible membrane can be held by and connected to the support structure using a number of fastening or anchoring mechanisms or arrangements, as long as, in the intended use of the apparatus, the membrane remains suspended from the support structure and hermetically seals the inflatable chamber. In some implementations, it may also be desirable that the support structure allows for the flexible membrane to be conveniently removed and reinstalled (e.g., following a rupture of the membrane or for cleaning the membrane). Furthermore, in some embodiments, the flexible membrane 28 may be intended to be releasably affixed to the support structure 26, which can allow the membrane 28 to be conveniently cleaned, replaced, repaired, repositioned, tighten or loosen, or otherwise serviced.

Referring still to FIGS. 3 to 5, in the illustrated embodiment, the flexible membrane 28 is clamped continuously along the entire periphery thereof by the peripheral frame 42, which can improve the strength of the connection and the integrity of the seal therebetween. However, in other embodiments, the periphery of the flexible membrane 28 may be connected to the support structure 26 at a plurality of discrete anchoring points, which can be regularly spaced or not, while maintaining inflatable chamber 32 hermetically sealed from the outside. It will be understood that by adjusting how the flexible membrane 28 is suspended from the support structure 26, it may be possible to adjust the value and/or the uniformity of the tension of the membrane 28. More details regarding how locally adjusting the tension of the flexible membrane can help achieving a semi-weight-bearing state when the foot is received on the membrane will be discussed further below.

Referring still to FIGS. 3 to 5, in the illustrated embodiment, the apparatus 20 may include an inflation unit 58 in fluid communication with the inflatable chamber 32. The inflation unit 58 is configured to selectively supply or discharge a pressurized fluid into or from the inflatable chamber 32, using valves or other suitable actuators, so as to regulate an internal pressure of the inflatable chamber 32 and, thereby, selectively inflate or deflate the inflatable chamber 32 and thereby adjust the pressure applied on the flexible membrane 28. In other words, when the inflatable chamber 32 is pressurized, the flexible membrane 28 can form an air cushion for receiving and supporting the foot in a semi-weight-bearing condition, as described further below. It is to be noted that the pressurized fluid is generally a gas, for example air, although the techniques described herein would not preclude the use of a liquid.

In some implementations, the inflation unit 58 can include a pressure sensor 80 (see, e.g., FIG. 3) in fluid communication with the inflatable chamber 32 for measuring the internal pressure in the inflatable chamber 32 which, in an embodiment, can be increased up to 5 kilopascals, although other internal pressure values may be used in other embodiments. It will be understood that the inflation unit 58 can be embodied using a variety of techniques, equipment and components known to those skilled in the art. Hence, its structure and operation need not be discussed in further detail herein.

Referring back to FIGS. 1 to 7, the apparatus 20 further includes a 3D imager 30, the 3D imager being provided under the flexible membrane 28 in order to acquire the topographical image of the plantar surface 22 when the foot 24 is disposed on the flexible membrane 28, as better illustrated in FIG. 4. As used herein, the term "3D imager" refers broadly to any component, device or system capable of acquiring a topographical image of the plantar surface when the foot is received on and supported by the flexible membrane. As mentioned above, the topographical image of the plantar surface of the foot provides a 3D model that replicates the plantar foot surface and generally consist of an array of data points, each designated by a spatial coordinate Z(x, y), where Z is the local height or elevation of the surface at position (x, y), generally measured from a reference plane of the 3D imager. It should be mentioned that, as used herein, the terms "light", "optical" and variants thereof are intended to refer to electromagnetic radiation in any appropriate region of the electromagnetic spectrum, and are not limited to visible light.

By way of example, in the illustrated embodiment, the 3D imager is a 3D laser scanner, such as the iQube™ scanner commercially available from Delcam Plc., Birmingham, UK. It will be appreciated, however, that various other conventional or specialized imaging devices, whether active or passive, may be used in other embodiments, depending on performance requirements or constraints of the device, for example in terms of its field of view, spatial resolution, sensitivity, image acquisition speed, size, weight, cost, and the like. Examples of suitable types of 3D imaging devices include, without limitation, 3D structured-light cameras, 3D time-of-flight cameras, 3D stereoscopic cameras, and other imaging devices capable of acquiring 3D depth images.

In the illustrated embodiment, the housing 48 is mounted onto the 3D imager 30, with the bottom wall 52 of the housing 48 in contact with the top surface 60 of the 3D imager. It will be understood that, in the illustrated embodiment, the 3D imager is configured to acquire the topographical image of the plantar surface 22 through the bottom wall 52 of the housing 48. Therefore, the bottom wall 52 of the housing 48 should be made of an optically transparent material (e.g., glass or another suitable material) on at least portion thereof sufficiently large to allow a topographical image of the entire plantar foot surface to be captured in one acquisition by the 3D imager 30.

Figure 8:
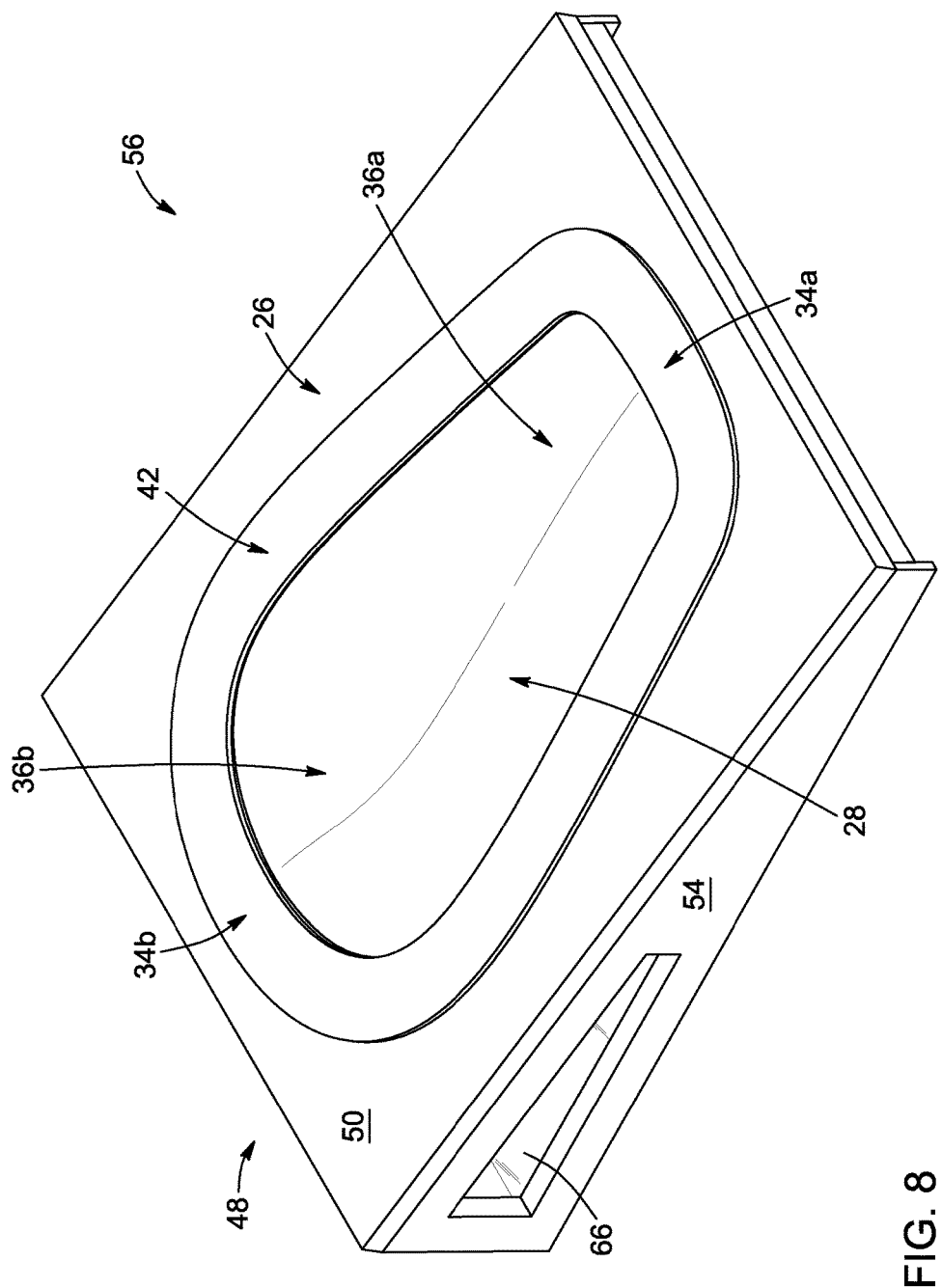
FIG. 8 is a schematic perspective view of a membrane assembly, in accordance with an embodiment.

It will be understood that, in the illustrated embodiment, the 3D imager 30 is releasably connected to the rest of the apparatus 20. In such a case, and referring to FIG. 8, the support structure 26 and the flexible membrane 28 suspended therefrom and defining an upper portion of the inflatable chamber 32 can define a membrane assembly 56 for use with, but manufactured independently of, the 3D imager 30.

Figure 15:
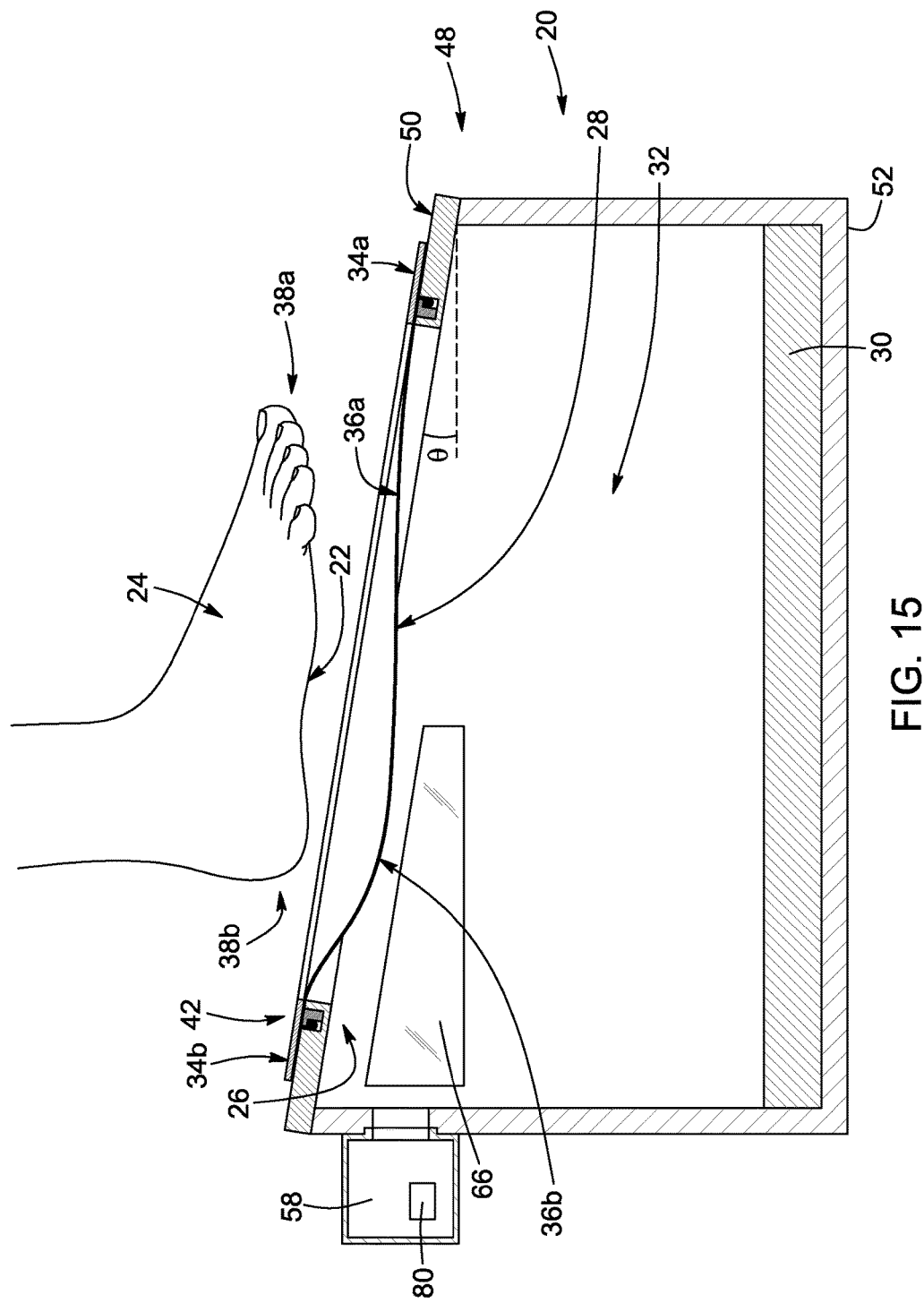
FIG. 15 is a schematic cross-sectional side view of an apparatus for obtaining a topographical image of a plantar surface of a foot, in accordance with another embodiment.

Referring to FIG. 15, in another embodiment, the 3D imager 30 may alternatively be positioned inside the housing 48, so that no part or component of the apparatus 20 is interposed between the 3D imager 30 and the flexible membrane 28. It will be understood that in such a case, the 3D imager 30 would be provided inside the inflatable chamber 32 and be formed integrally with the other components of the apparatus 20.

In an embodiment, the flexible membrane may be partially or fully opaque to the optical radiation used by the 3D imager, in which case the 3D imager actually acquires an image of the flexible membrane deformed by the foot received thereon. However, in another embodiment, the flexible membrane may be optically transparent to the optical radiation used by the 3D imager, so that the image of the plantar surface itself is acquired by the 3D imager.

As mentioned above, a general aim of the techniques described herein consists in controlling the forces exerted on the forefoot by the membrane, in order to reduce the deformation of the forefoot which, if significant, can have repercussions on the overall shape of the plantar surface and, potentially, degrade the reliability and accuracy of the 3D plantar image. In particular, it is desirable that the toes are neither excessively dorsiflexed (i.e., not overly curled up) nor forming "artificial" lateral arches (i.e., either concave or convex), so as to ensure that the medial and lateral arches, whose shape is to be acquired, are not adversely deformed. At the same time, a certain amount of deformation in the rear foot region may be beneficial, especially as it can allow the 3D plantar image to be more representative of the natural physiological deformation of the medial and lateral arches. As will now be described, in the techniques described herein, the control of the forces exerted on and deformation experienced by the foot may be achieved by carefully selecting the structure and configuration of the flexible membrane and/or the support structure including the opening.

Referring to FIGS. 1 to 7, and more particularly to FIG. 4, in the techniques described herein, the flexible membrane 28 is configured to receive and support alone and autonomously the foot 24. Stated otherwise, during the acquisition of the topographical plantar image, the entire plantar surface of the foot 24 is supported solely by the inflatable suspended flexible membrane 28, without contact with other physical parts or components of the apparatus 20. This condition can be achieved, for example, by properly selecting the shape and the elasticity of the flexible membrane 28, as well as the configuration in which it is suspended from the support structure 26 (e.g., the inclination of the membrane 18 due to the rear end 34b of the support structure 26 being elevated relative to the front end 34a thereof).

In contrast to certain known systems (see, e.g., U.S. Pat. No. 7,392,559), in the present apparatus 20, when the foot 24 is placed on the flexible membrane 28 and the inflatable chamber 32 is pressurized, the membrane 28 does not become stretched to such an extent that the front portion 38a of the foot 24 impinges on and bears against an underlying solid surface (e.g., the bottom wall 52 of the housing 48 in FIG. 4) while the rear portion 38b of the foot 12 remains suspended. Indeed, if the front portion 38a of the foot were to abut against the bottom wall 52 of the housing 48 during the image acquisition process, the resulting deformation of the front portion 38a of the foot 24 would create a full-weight-bearing condition and improper deformation of the overall plantar surface 22, which could in turn negatively affect the reliability of the acquired image data. Hence, in the embodiment of FIGS. 1 to 7, the vertical separation between the suspended membrane 28 and the bottom wall 52 is such that no portion of the foot 24 will impinge on and bear against the bottom wall 52 when the foot 24 is received on the flexible membrane 28 and the pressure inside the inflatable chamber 32 is raised to a value that produces a semi-weight-bearing condition, for example, and without limitation, between 3 and 7 kilopascals.

Referring still to FIGS. 1 to 7, in addition to being configured for supporting the entire plantar surface 22 of the foot 24 alone and unaided by another physical component, the flexible membrane 28 is configured such that the rearfoot-receiving region 36b is under less tension than the forefoot-receiving region 36a. Indeed, it will be understood that by having a higher tension in the forefoot-receiving region 36a than in the rearfoot-receiving region 36b the deformation undergone by the front portion 38a of the foot 24 will be smaller than that undergone by the rear portion 38*b*, thus making it easier for the foot 24 to reach a semi-weight-bearing condition.

As will now be described, a non-uniform tension in the flexible membrane 28 can be achieved by adjusting the physical properties of the flexible membrane 28 itself and/or the manner by which it is suspended from the support structure 26 (e.g., whether the tension imposed on the membrane 28 by the support structure 26 is uniform or not).

Figure 6:
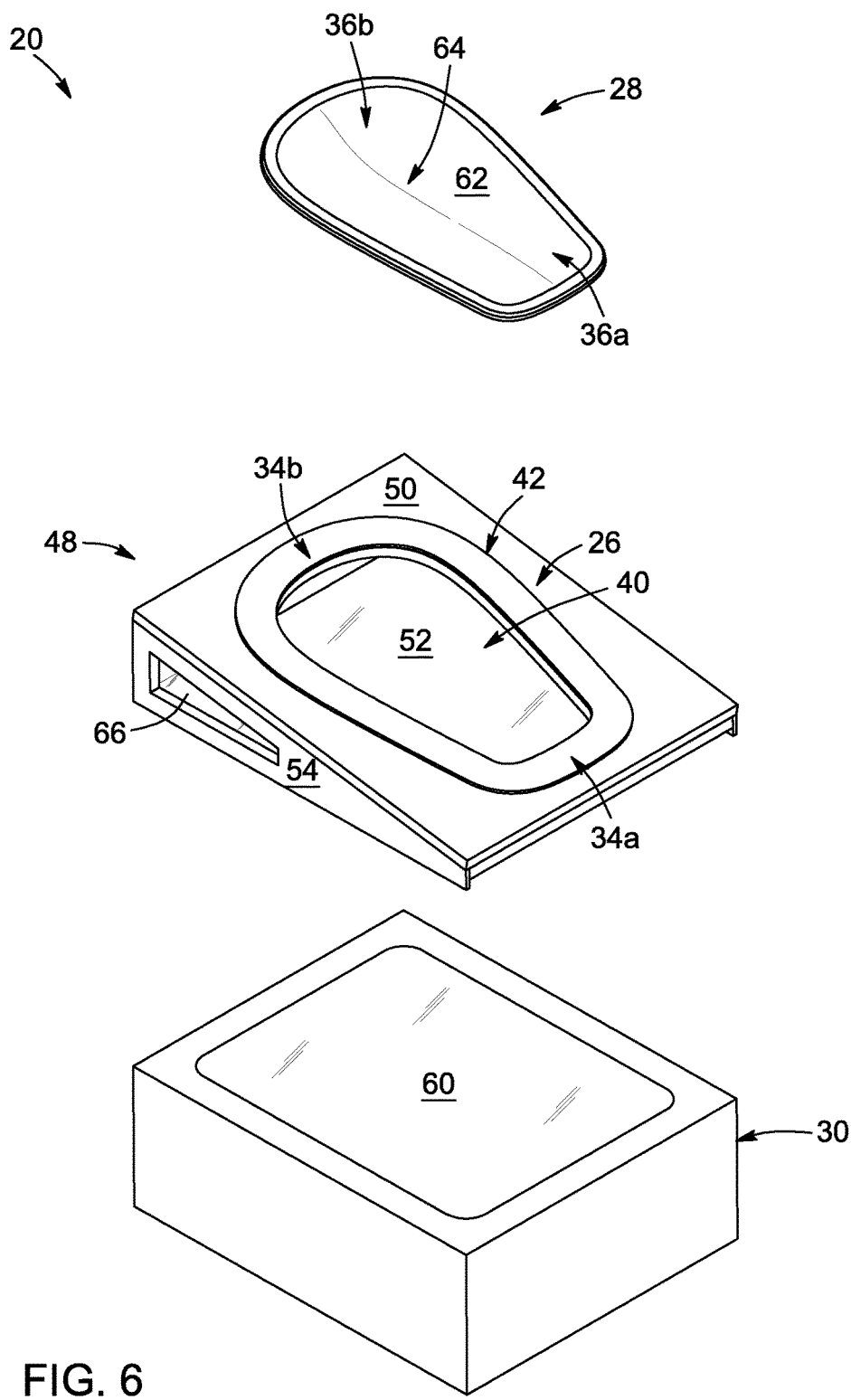
FIG. 6 is a partially exploded perspective view of the apparatus of FIG. 1.
Figure 7:
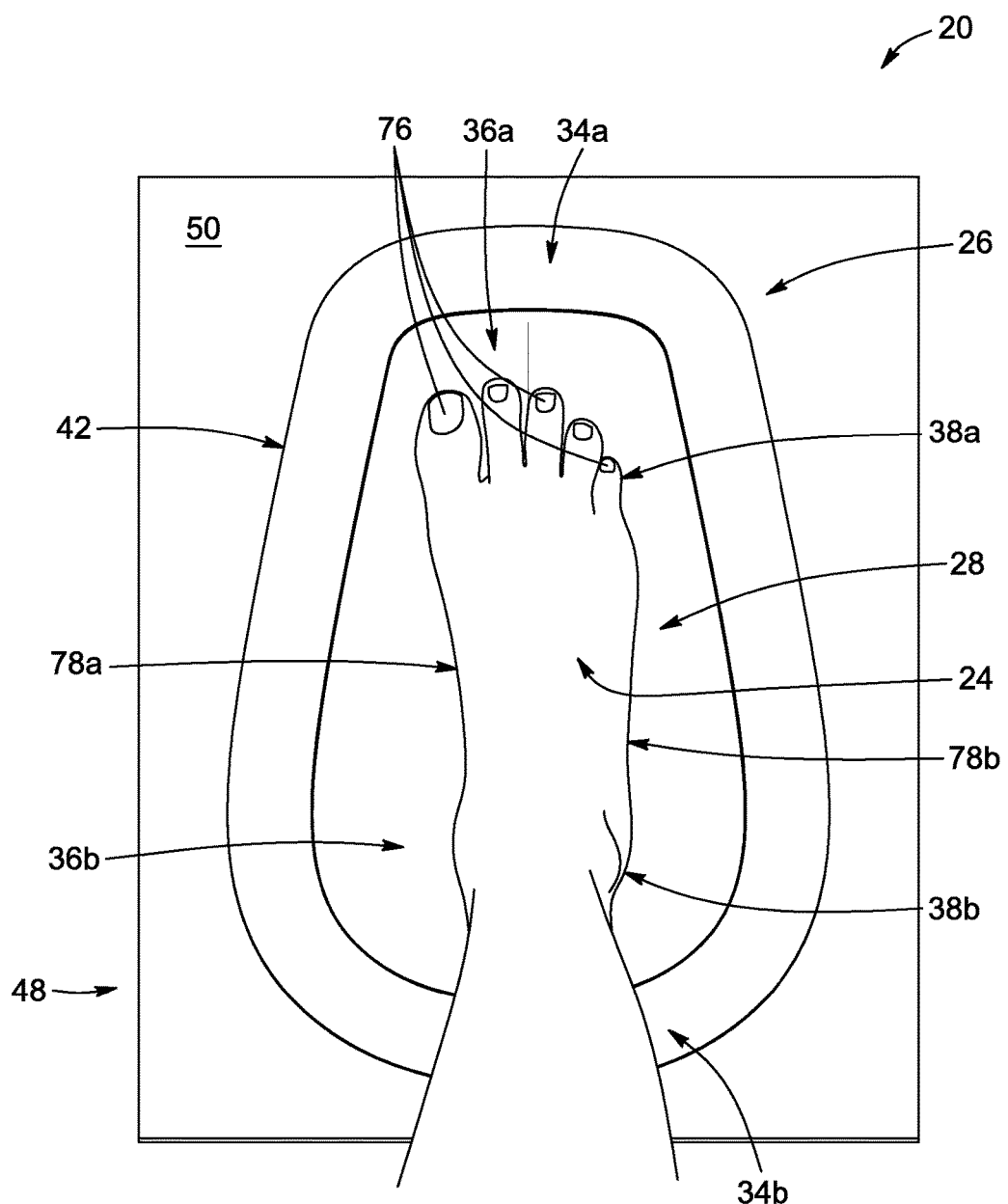
FIG. 7 is a top plan view of FIG. 1, with a foot received on the flexible membrane.

Referring more specifically to FIGS. 5 and 6, in the illustrated embodiment, the flexible membrane 28 is preformed so that its upper surface 62 includes an upwardly concave recessed area 64 formed in the rearfoot-receiving region 36*b*. As used herein, the term "preformed" is used to indicate that the flexible membrane has been subjected, prior to being affixed to the support structure, to a manufacturing process to confer to the flexible membrane a form having a predetermined size and shape and, generally, a non-flat cross-section. The term "preformed" also refers to the fact that the flexible membrane retains shape conferred thereto when disposed on a flat surface. Of course, since it is made of an elastic material, the flexible membrane will nevertheless be deformed when a sufficient load is applied thereto (e.g., the weight of a foot).

Referring still to FIGS. 5 and 6, in the illustrated embodiment, the flexible membrane 28 is under less tension in the rearfoot-receiving region 36*b* than in the forefoot-receiving region 36*a* as a result of the extra "slack" or "looseness" deliberately introduced in the rearfoot-receiving region 36*b* by the concave recessed area 64. It is noted that in the illustrated embodiment, the width of the membrane 28 is greater in the rearfoot-receiving region 36*b* than in the forefoot-receiving region 36*a* due not only to the slack or looseness created by the concave recessed area 64, but also to the fact that the width of the opening 40 enclosed by the peripheral frame 42, and across which is supported the flexible membrane 28, has a width that increases from the front end 34*a* toward the rear end 34*b* of the support structure 26.

Referring to FIG. 10, in another embodiment, a semi-weight-bearing condition may be achieved with a flexible membrane 28 preformed to be less tensioned in the rearfoot-receiving region 36*b*, but with the opening 40 enclosed by the peripheral frame 42 having a substantially uniform width.

Figure 9:
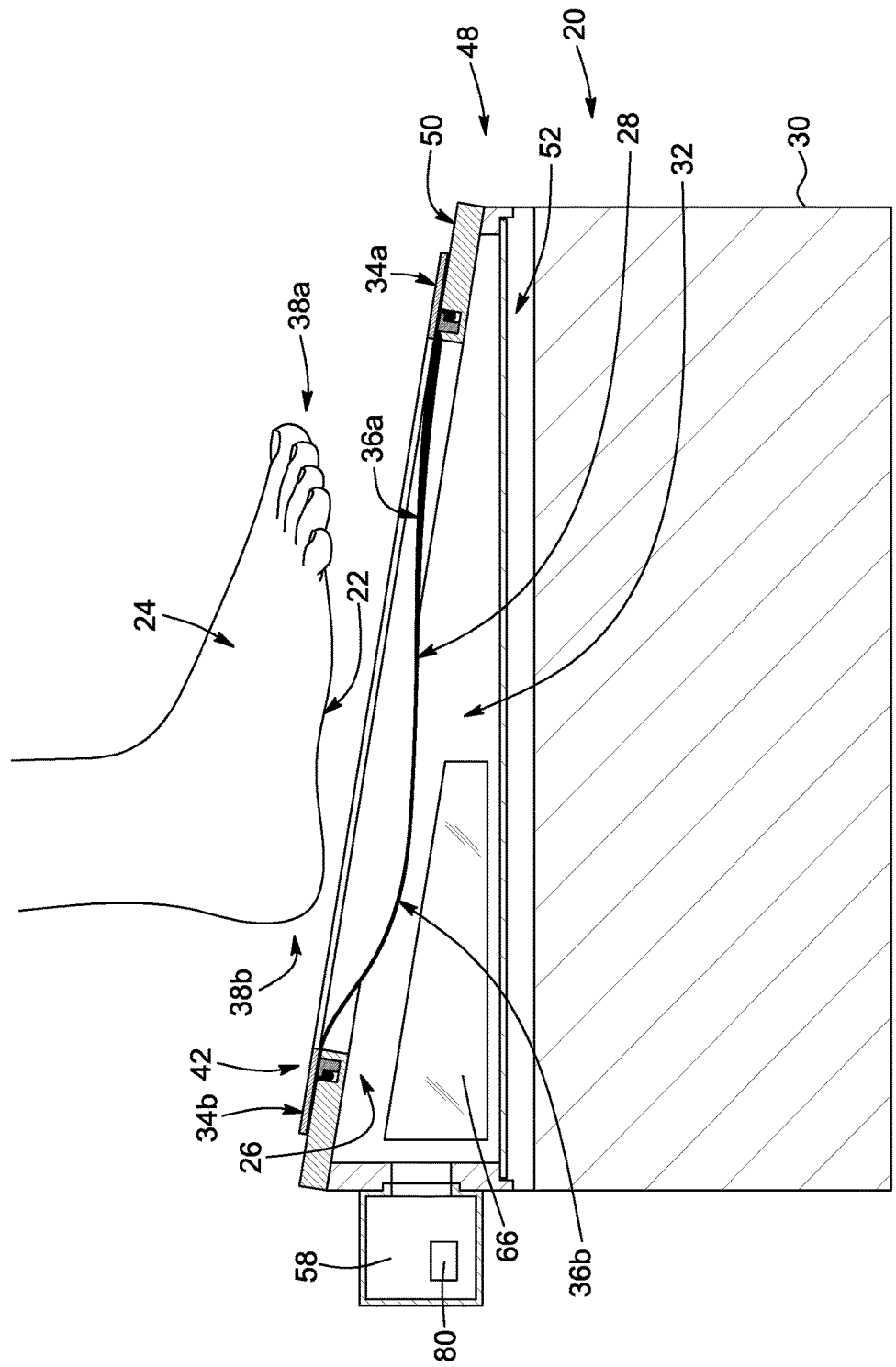
FIG. 9 is a cross-sectional side view of an apparatus for obtaining a topographical image of a plantar surface of a foot, in accordance with another embodiment.

Referring to FIG. 9, in still another embodiment, the tension in the flexible membrane 28 may be controlled by providing the membrane 28 with a non-uniform thickness. In particular, in the embodiment of FIG. 9, the membrane has a thickness greater in the forefoot-receiving region 36*a* than in the rearfoot-receiving region 36*b*, thereby increasing the tension in the former compared to the latter.

Figure 2:
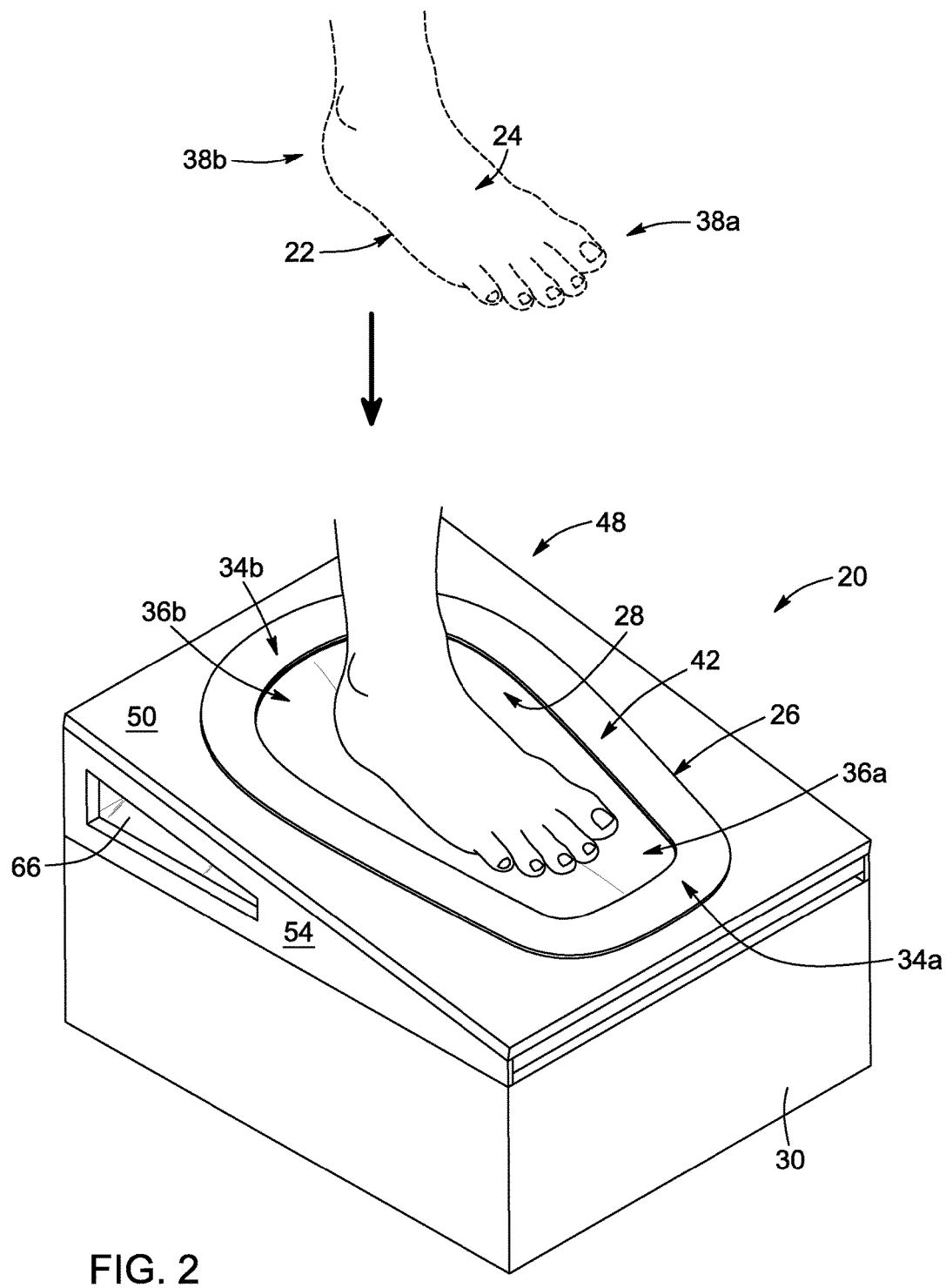
FIG. 2 is the same as FIG. 1, but with a foot received on the flexible membrane.
Figure 16A:
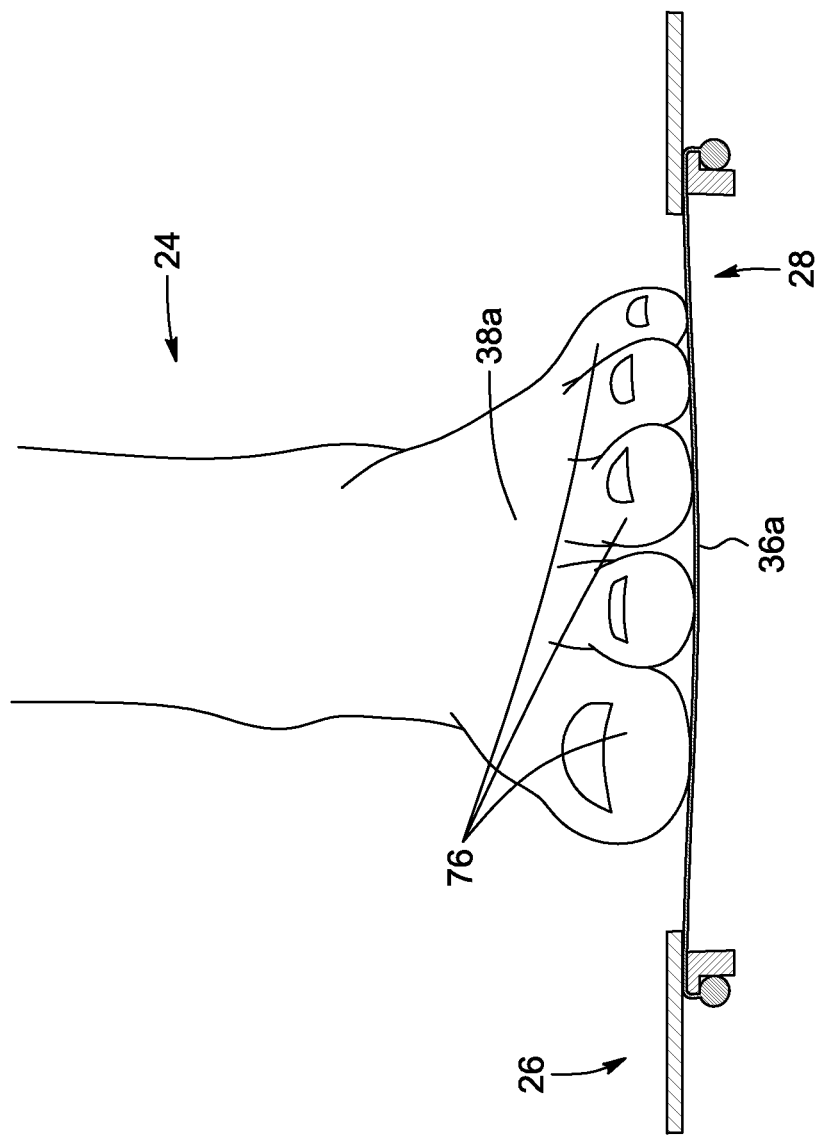
FIG. 16A is a schematic, simplified front view of the apparatus of FIG. 2.
Figure 16B:
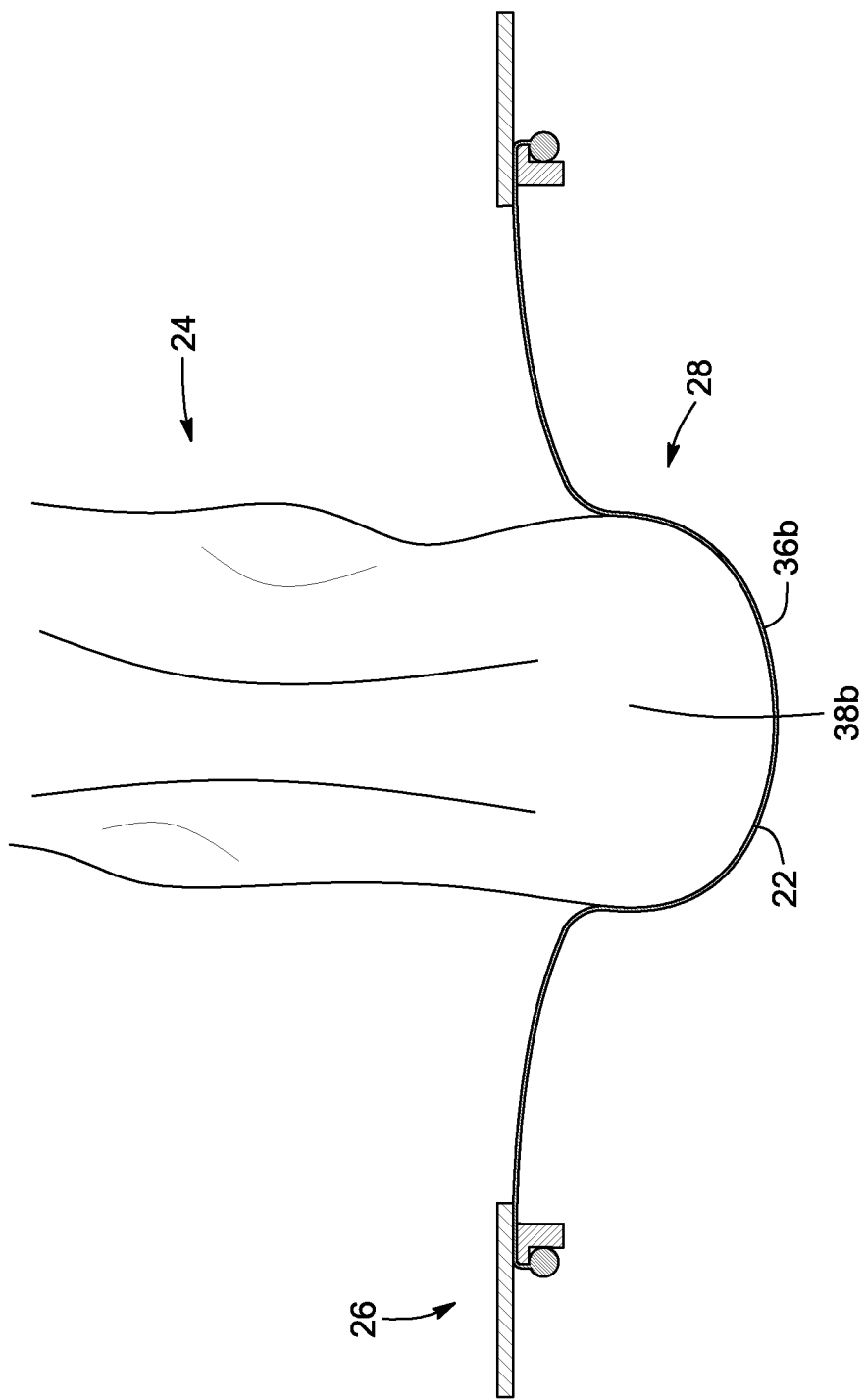
FIG. 16B is a schematic, simplified rear view of the apparatus of FIG. 2.

Turning now FIGS. 16A and 16B, there are shown a front view and a rear view, respectively, of the apparatus 20 depicted in FIG. 2, which illustrate that the front portion 38*a* and the rear portion 38*b* of the foot 24 are under different conditions when received on the flexible membrane 28. First, referring to FIG. 16A, it can be seen that the forefoot-receiving region 36*a* of the flexible membrane 28 is under relatively high tension and presents a rather uniform and flat receiving surface to the front portion 38*a* of the foot 24. As a result, the deformation of the front portion 38*a* of the foot 24 due to either vertical or lateral compressive loads remains relatively small. In particular, turning briefly to FIG. 7, the toes 76 are neither overly curled up nor forming artificial lateral arches, which otherwise would negatively impact the measurements of the medial and lateral arches 78*a*, 78*b*. Second, referring to FIG. 16B, the rearfoot-receiving region 36*b* is under reduced tension and receives the rear portion 38*b* of the foot 24 in the concave recessed area 64. As a result, the rearfoot-receiving region 36*b* of the flexible membrane 28 produces larger lateral and vertical compressive forces and envelops the foot 12 more than does the forefoot-receiving region 36*a* (see FIG. 16A). It will be understood that in such a configuration, the foot 24 can be placed more readily in a semi-weight-bearing condition.

Referring still to FIGS. 1 to 7, it is often desirable that, in a semi-weight-bearing state, the upwardly directed reaction force acting on the foot 24 in response to the downwardly directed force exerted by the foot 24 received on the flexible membrane 28 be as uniform as possible over the foot plantar surface 22. In a non-limitative embodiment, the patient may be in a sitting position when he or she places his or her foot 24 on the flexible membrane 28. This configuration generally results in the force exerted by the rear portion 38*b* of the foot 24 on the rearfoot-receiving region 36*b* of the flexible membrane 28 being greater than the force exerted by the front portion 38*a* of the foot 24 on the forefoot-receiving region 36*a* of the flexible membrane 28, due to the additional downwardly directed force generally applied by the podiatric physician on the patient's knee. It will be understood that by providing the rear end 34*b* of the support structure 26 higher than the front end 34*a* such as to suspend the membrane 28 at an inclination angle, it may be possible to compensate at least partially for this excess of force acting on the rear portion 38*b* of the foot 24. As a result, the plantar surface 22 of the foot 24 may advantageously be oriented substantially parallel to the image plane of the 3D imager 30 during the image acquisition procedure.

Figure 12:
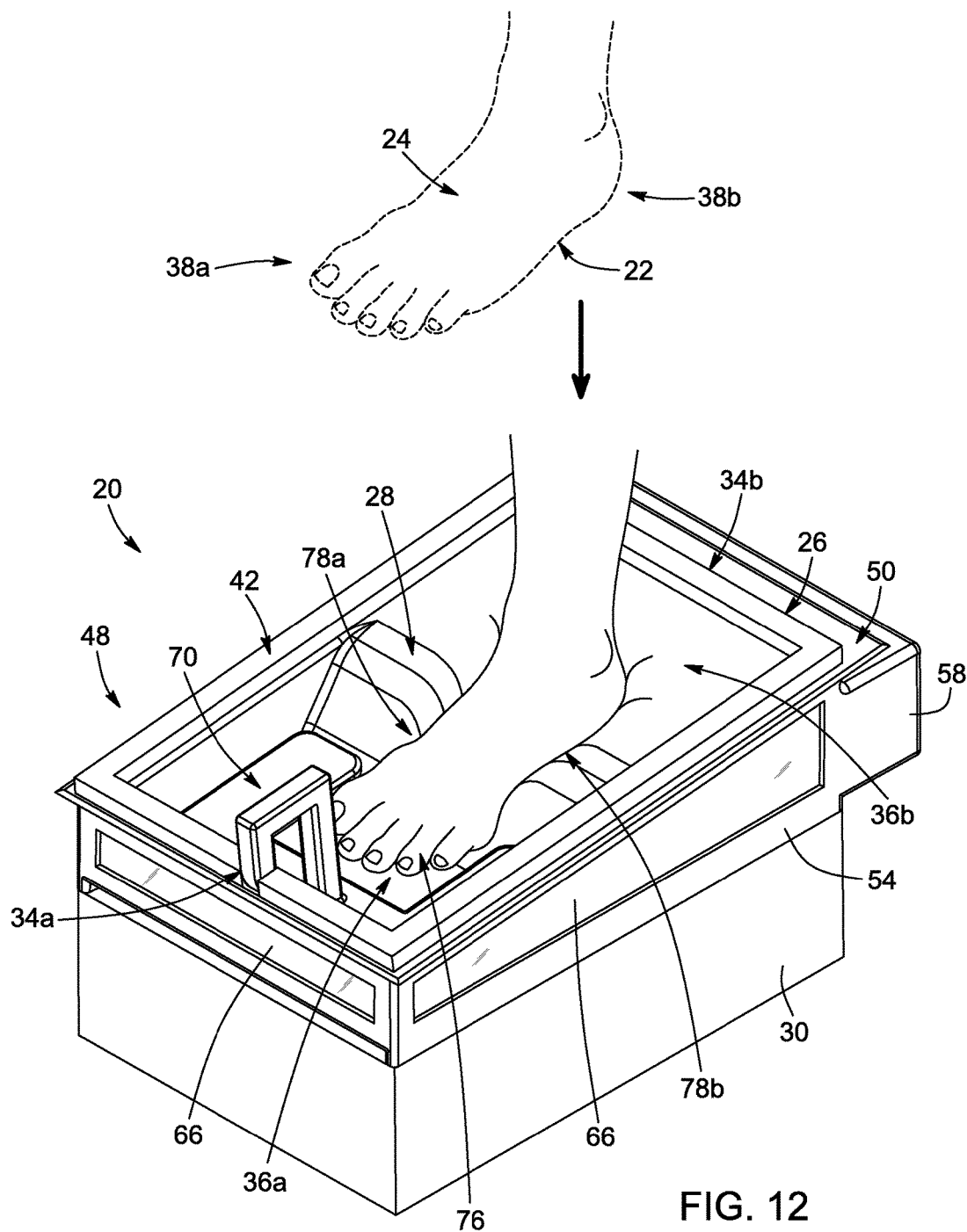
FIG. 12 is the same as FIG. 11, but with a foot received on the flexible membrane.
Figure 13:
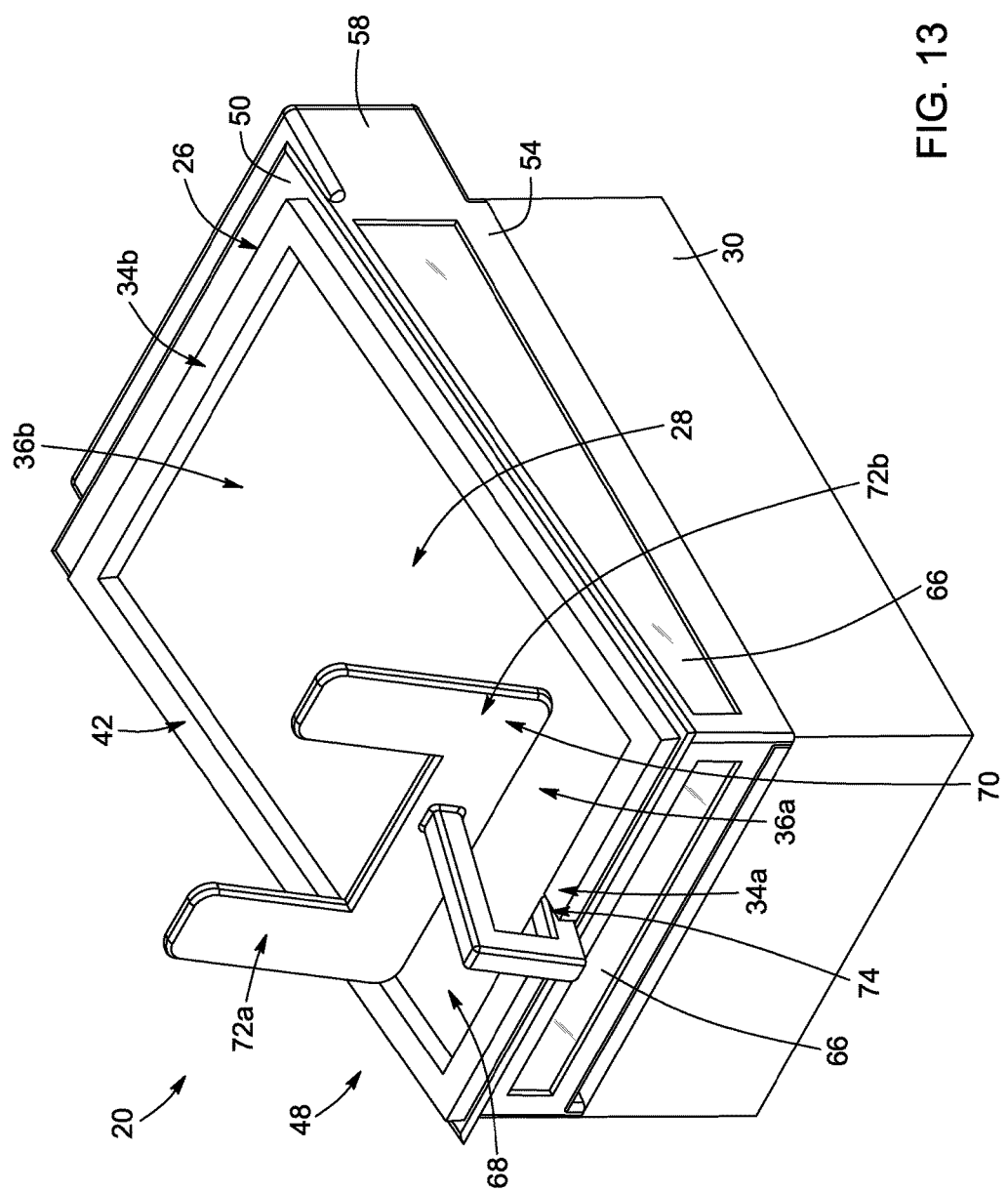
FIG. 13 is the same as FIG. 11, but with the tension member pivoted from an operative to an inoperative position.
Figure 14:
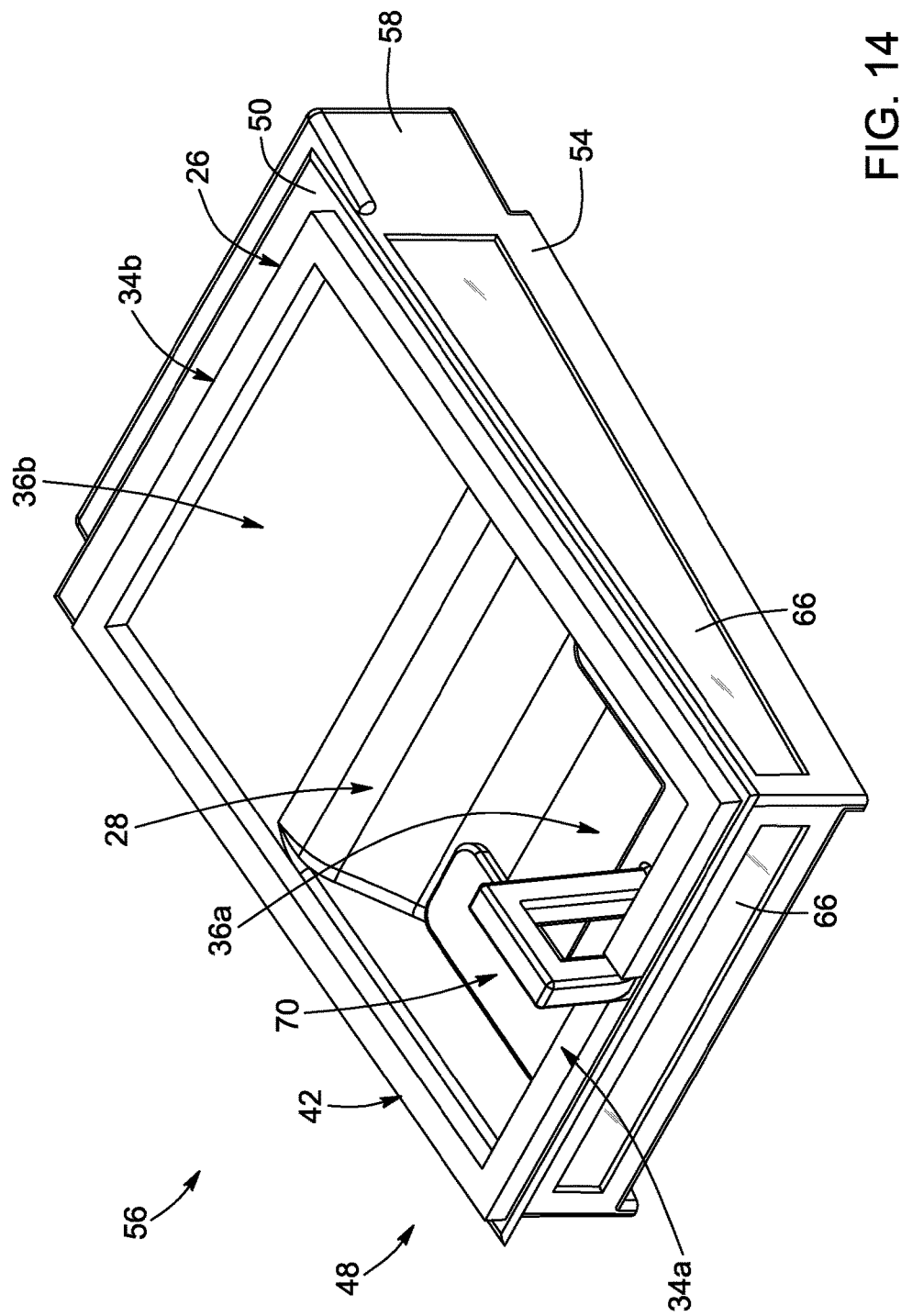
FIG. 14 is a schematic perspective view of a membrane assembly, in accordance with another embodiment.

Referring now to FIGS. 11 to 13, there is illustrated another embodiment of an apparatus 20 for a topographical image of a plantar surface 22 of a foot 24 in a semi-weight-bearing condition. As for the embodiment of FIGS. 1 to 7, the apparatus 20 in FIGS. 11 to 13 includes a support structure 26 having a front end 34*a* and a rear end 34*b* elevated relative to the front end 34*a*, a flexible membrane 28 suspended from the support structure 26 and configured to receive and support the entire plantar surface 22 of the foot 24 thereon, and a 3D imager 30 provided under the flexible membrane 28 in order to acquire the topographical image of the plantar surface 22 when the foot 24 is disposed on the flexible membrane 28. The flexible membrane 28 defines and encloses an upper portion of an inflatable chamber 32, and includes a forefoot-receiving region 36*a* and a rearfoot-receiving region 36*b*, where the rearfoot-receiving region 36*b* is under less tension than the forefoot-receiving region 36*a*. FIG. 14 is a membrane assembly 56 which can be used with a 3D imager to form an apparatus such as that illustrated in FIGS. 11 to 13.

In contrast to the embodiment of FIGS. 1 to 7, in the embodiment of FIGS. 11 to 13, the difference in tension between the forefoot-receiving region 36*a* and the rearfoot-receiving region 36*b* is not achieved by preforming the flexible membrane 28. Rather, the difference in tension is achieved by anchoring the flexible membrane 28 non-uniformly along the peripheral frame 42 of the support structure 26 so as to create a "slack" or "looseness" in the rearfoot-receiving region 36*b*. By way of example, in an embodiment, this can be achieved first by placing the flexible membrane 28 on a preformed surface (not shown) in such a way as to make the rearfoot-receiving region 36*b* looser than the forefoot-receiving region 36*a*. Then, while still located on the preformed surface, the flexible membrane 28 can be affixed to the peripheral frame 42 forming the support structure 26 in a manner such as to maintaining looseness in the rearfoot-receiving region 36*b*. Finally, the support structure 26 with the flexible membrane 28 affixed thereto can be installed on the top wall 50 of the housing 48.

Referring still to FIGS. 11 to 13, the apparatus 20 further includes a tension member 70 configured to be urged against and exert a downwardly directed force on a peripheral portion 68 of the forefoot-receiving region 36*a* of the flexible membrane 28. In the illustrated embodiment, the tension member 70 is U-shaped and includes two legs 72*a*, 72*b* between which can be received the front portion 38*a* of the foot 24 (see FIG. 12). The tension member 70 may, but need not, be made of a transparent material so as not to interfere with the image acquisition process. Furthermore, in the illustrated embodiment, the tension member 70 is pivotable about a pivot axis 74 between an operative position, where the tension member 70 is urged against and exerts the downwardly directed force onto the peripheral portion 68 of the forefoot-receiving region 36*a* of the membrane 28, and an inoperative position, where the tension member 70 is pivoted away from the membrane 28.

Referring still to FIGS. 11 to 13, when tension member 70 is in the operative position, it is pushed against the flexible membrane 28, thereby increasing the slope between the forefoot-receiving region 36*a* and the rearfoot-receiving region 36*b*. It will be understood that the tension member 70 acts to increase the tension applied to the membrane 28 in the forefoot-receiving region 36*a*, which in turn, reduces the pressure on and the deformation experienced by the front portion 38*a* of the foot 24 when supported by the flexible membrane 28 in a semi-weight-bearing condition (see FIG. 12). This reduction in pressure on and deformation of the front portion 38*a* of the foot 24 ensures that the toes 76 are not overly curled up, which otherwise could adversely deform the medial and lateral arches 78*a*, 78*b* of the foot 24 and render the image acquisition process difficult and imprecise. It is to be noted that as for the embodiment described above in connection with FIGS. 1 to 7, the entire plantar surface 22 of the foot 24 is supported by the membrane 28 in the embodiment of FIGS. 11 to 13, without any part of the foot 24 being in contact with or supported by a solid surface provided below the flexible membrane 28.

Method

Figure 17:
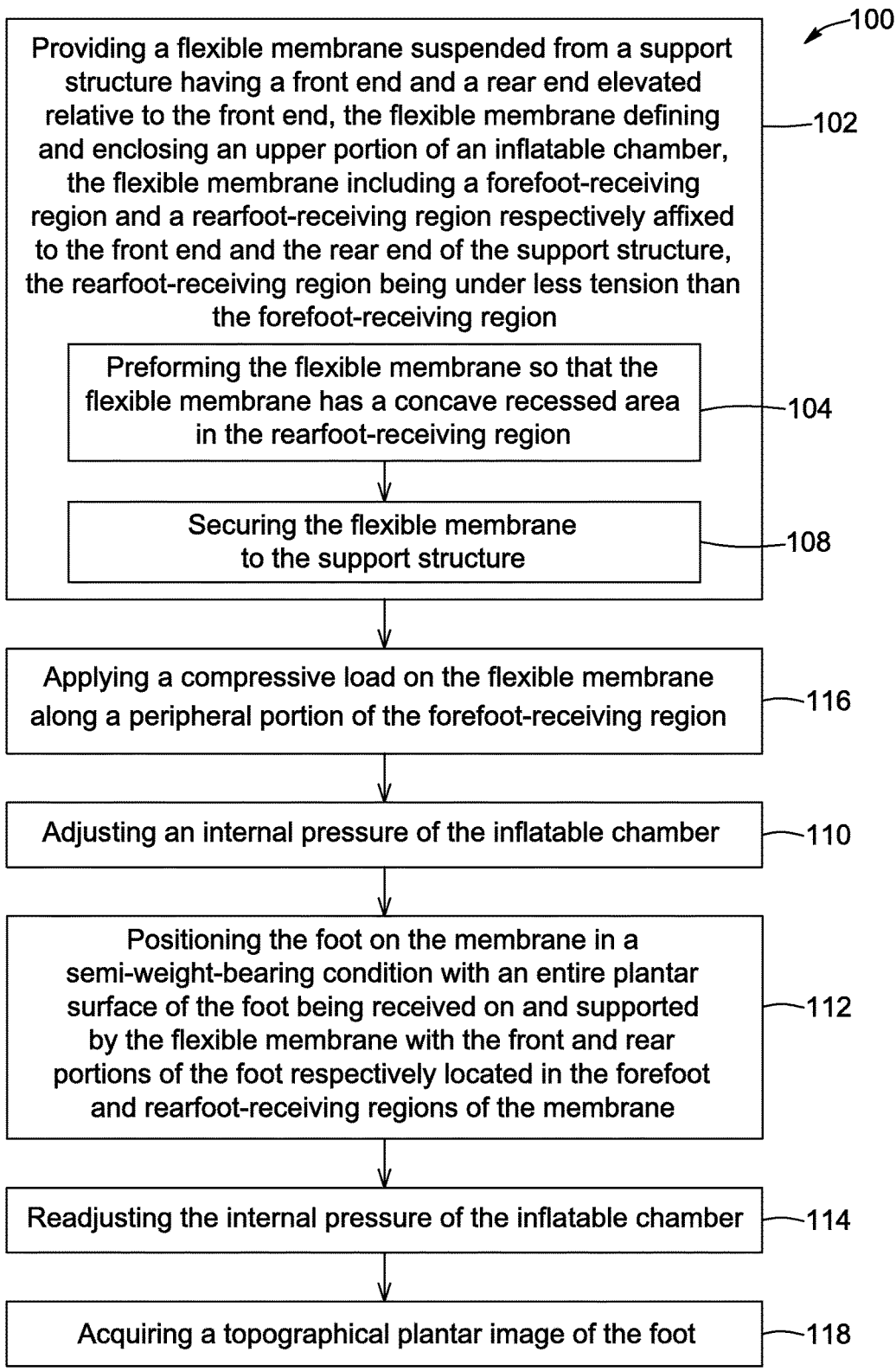
FIG. 17 is a flow chart of a method for imaging a foot having a front portion and a rear portion, in accordance with a first exemplary embodiment.

In accordance with another aspect, there is provided a method for imaging a plantar surface of a foot having a front portion and a rear portion. Referring to FIG. 17, there is provided a flow chart of an exemplary embodiment of such a method 100. By way of example, the method 100 shown in FIG. 17 and described herein can be performed with an apparatus such as those illustrated in FIG. 1 to 7, 9, 10, 11 to 13 or 15, or another apparatus.

Referring to FIG. 17, in a first step 102, a flexible membrane, suspended from a support structure and enclosing an upper portion of an inflatable chamber, is first provided. The flexible membrane has a front end and a rear end, elevated relative to the front end. The flexible membrane includes a forefoot-receiving region and a rearfoot-receiving region respectively affixed to the front end and the rear end of the support structure. The rearfoot-receiving region is under less tension than the forefoot-receiving region.

Figure 18:
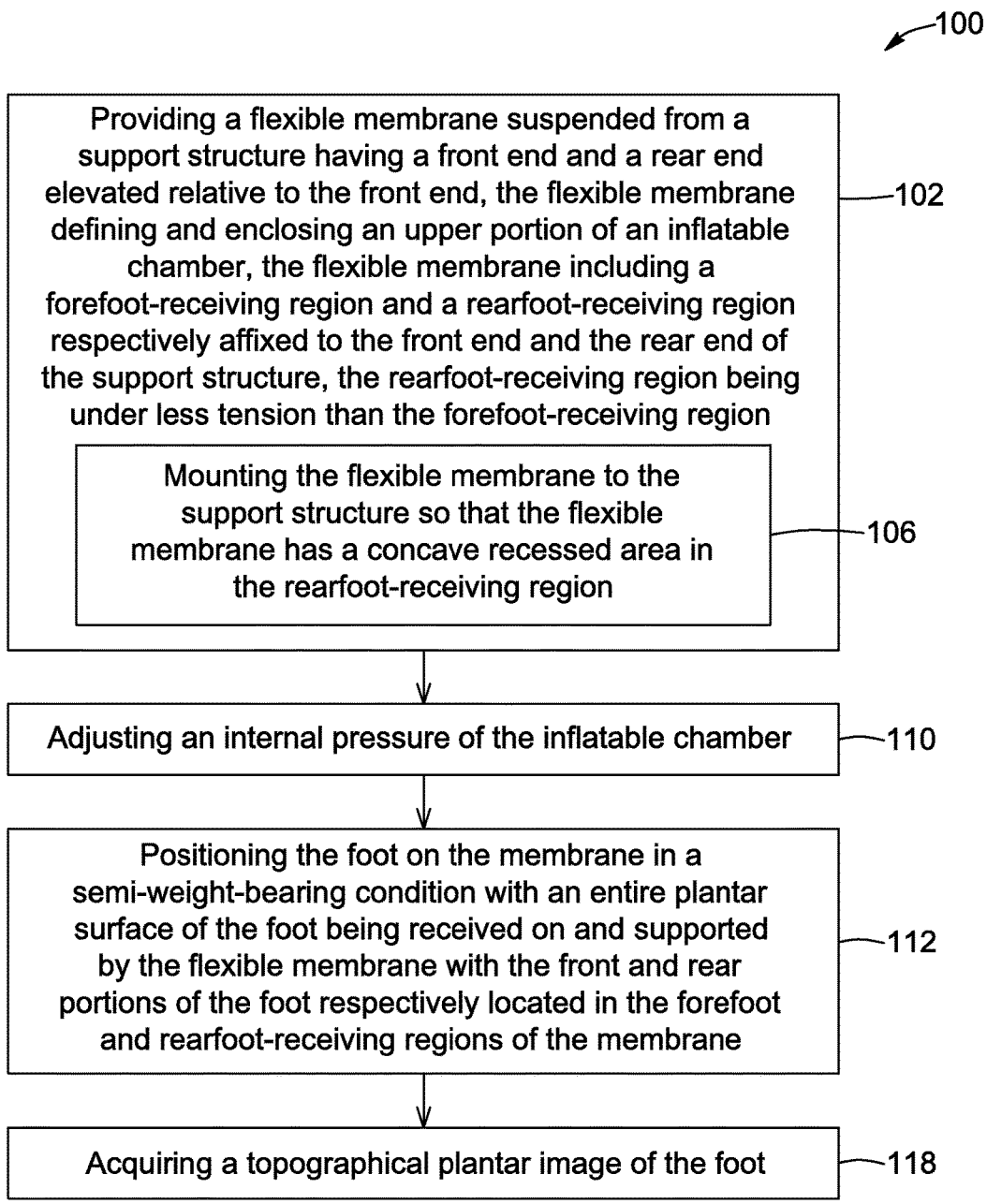
FIG. 18 is a flow chart of a method for imaging a foot having a front portion and a rear portion, in accordance with a second exemplary embodiment.

In some implementations, the step 102 of providing the flexible membrane suspended from the support structure includes a step 104 of preforming the flexible membrane so that the flexible membrane has a concave recessed area in the rearfoot-receiving region and, consequently, having the rearfoot-receiving region under less tension than the forefoot-receiving region. Alternatively, referring to FIG. 18, which provides another exemplary embodiment of the method 100, the step 102 of providing the flexible membrane suspended from the support structure can include a step 106 of mounting the flexible membrane to the support structure so that the flexible membrane has a concave recessed area in the rearfoot-receiving region.

Referring back to FIG. 17, in some implementations, the step 102 of providing the flexible membrane includes a step 108 of securing the flexible membrane to the support structure.

Then, internal pressure in the inflatable chamber is increased at step 110. Internal pressure can be increased by blowing gas, such as air, in the inflatable chamber.

In some implementations, the step 110 of increasing the pressure in the inflatable chamber is carried out until an internal pressure threshold is reached. The value of the internal pressure threshold can be determined such as to induce a deformation of the foot received on the flexible membrane that leads to a semi-weight-bearing state in which the foot arch and the heel are properly enveloped by the flexible membrane. The internal pressure threshold can be determined by the podiatric physician manually sensing the internal pressure in the pressure chamber or based on pressure data provided by a pressure sensor operatively connected to the inflatable chamber. The internal pressure threshold can also be predetermined, based on, for example and without being limited to, patient's characteristics, the elasticity of the membrane and/or the inclination angle of the suspended membrane. For instance, the apparatus can include a pressure sensor operatively connected to the inflatable chamber, a controller operatively connected to the pressure sensor and a blower, for instance, configured to blow gas in the inflatable chamber. Using pressure data provided by the pressure sensor, the controller can control the blower and, more particularly, stop gas injection in the inflatable chamber when the predetermined internal pressure threshold is reached.

Then, when the inflatable chamber is under pressure, the method 100 includes a step 112 in which the patient's foot is positioned on the flexible membrane in a semi-weight-bearing condition with the front and rear portions of the foot respectively located in the forefoot and rearfoot-receiving regions of the membrane, that is, with the entire plantar surface of the foot supported by the flexible membrane, without contact with other physical parts or components.

In some implementations, the patient's foot is positioned on the flexible membrane by the podiatric physician. The podiatric physician manipulates the patient's foot to ensure that the latter is configured in the semi-weight-bearing condition. By way of example, in a non-limitative embodiment, the podiatric physician can perform one or more of the following manipulations: (i) moving the foot vertically downwardly onto the membrane with the front and the rear portions of the foot received in the forefoot- and rearfoot-receiving regions of the membrane, respectively; (ii) setting at or near 90 degrees each one of the angle between the foot and the tibia, the angle between the tibia and the femur and the angle between the femur and the torso, while keeping the foot, the tibia and the femur in a same vertical plane; (iii) adjusting the internal pressure inside the inflatable chamber based on the rigidity of the foot; (iv) positioning the subtalar joint in a neutral position; (v) exerting a downwardly directed force on the patient's knee to achieve a desired semi-weight-bearing state; and (vi) maintaining the desired semi-weight-bearing state while acquiring the 3D plantar image.

In some implementations, following an initial positioning of the patient's foot on the flexible membrane, the method 100 can include a step 114 in which the pressure in the inflatable chamber can be adjusted, that is, it can either be decreased or increased. The pressure in the inflatable chamber can be adjusted manually by the podiatric physician or automatically. Further positioning of the patient's foot on the flexible membrane can be performed following adjustment of the internal pressure of the inflatable chamber. The steps of positioning 112 of the patient's foot on the flexible membrane and adjusting 110 the internal pressure of the inflatable chamber can be carried out as an iterative process until the position of the patient's foot on the flexible membrane in the semi-weight-bearing condition is satisfactory.

In some implementations, the step 112 of positioning the patient's foot on the flexible membrane can include exerting a downwardly directed force on the foot when the foot is received on the flexible membrane. For instance, the downwardly directed force can be applied by the podiatric physician while maintaining the patient's foot in the semi-weight-bearing condition.

In some implementations, either prior to inflating the inflatable chamber or the initial positioning of the patient's foot on the flexible membrane or the initial positioning of the patient's foot on the flexible membrane, the method can include a step 116 of applying a compressive load on the flexible membrane along a peripheral portion of the forefoot-receiving region. For instance, in an embodiment such as that illustrated in FIGS. 11 to 13, it can include configuring the tension member 70 in the operative position to increase the tension applied on the forefoot-receiving region 36a of the flexible membrane 28.

Then, referring back to FIG. 17, when the patient's foot is positioned on the flexible membrane in the semi-weight-bearing condition, the method includes a step 118 of acquiring a topographical image of the plantar surface of the foot and saving the acquired plantar surface data on a data support. In a non-limiting embodiment, the 3D imager is manually activated by the podiatric physician.

As mentioned above, the topographical plantar image can be used to design and manufacture a patient-specific orthosis.

Of course, numerous modifications could be made to the embodiments described above without departing from the scope of the present invention.

What is claimed is:

1. A membrane assembly for use with a three-dimensional imager to obtain a topographical plantar image of a foot, the membrane assembly comprising:

a housing comprising a top wall having an opening formed therethrough, a bottom wall configured to be positioned on the three-dimensional imager, the bottom wall being optically transparent on at least a portion thereof, a sidewall interconnecting the top wall and the bottom wall, and a support structure connected to the top wall along a periphery of the opening, the support structure having a front end and a rear end, the rear end being elevated relative to the front end; and a flexible membrane to receive thereon the foot, the flexible membrane suspended from the support structure and extending across and sealing the opening, the flexible membrane including a forefoot-receiving region and a rearfoot-receiving region respectively adjacent to the front end and the rear end of the support structure, the rearfoot-receiving region being under less tension than the forefoot-receiving region, the flexible membrane and the housing defining an inflatable chamber, the flexible membrane configured, upon inflation of the inflatable chamber, to inflate and to support an entire plantar surface of the foot in a spaced-apart and contactless relationship with the bottom wall of the housing, the three-dimensional imager configured to acquire the topographical plantar image through the optically transparent portion of the bottom wall.

2. The membrane assembly according to claim 1, wherein the flexible membrane has a thickness greater in the forefoot-receiving region than in the rearfoot-receiving region.

3. The membrane assembly according to claim 1, wherein the flexible membrane comprises a concave recessed area in the rearfoot-receiving region.

4. The membrane assembly according to claim 3, wherein the flexible membrane is preformed with a predetermined shape to provide the concave recessed area in the rearfoot-receiving region.

5. The membrane assembly according to claim 1, wherein the flexible membrane has a width greater in the rearfoot-receiving region than in the forefoot-receiving region.

6. The membrane assembly according to claim 1, wherein the opening formed in the top wall has a width that increases from the front end toward the rear end of the support structure.

7. The membrane assembly according to claim 1, wherein the opening formed in the top wall has a uniform width.

8. The membrane assembly according to claim 1, wherein an elevation angle of the rear end with respect to the front end is between 5 degrees and 30 degrees.

9. The membrane assembly according to claim 1, wherein the flexible membrane is uniformly connected to the support structure along the periphery of the opening formed in the top wall.

10. The membrane assembly according to claim 1, wherein the top wall is inclined at a slope angle relative to the bottom wall.

11. The membrane assembly according to claim 1, further comprising an inflation unit in fluid communication with the inflatable chamber, the inflation unit being configured to regulate an internal pressure in the inflatable chamber.

12. The membrane assembly according to claim 11, wherein the inflation unit comprises a pressure sensor in fluid communication with the inflatable chamber for measuring the internal pressure in the inflatable chamber.

13. The membrane assembly according to claim 1, further comprising a tension member connected to the housing and configured, upon inflation of the inflatable chamber, to be in an operative position wherein the tension member is urged against and exerts a downwardly directed force on a peripheral portion of the forefoot-receiving region of the flexible membrane.

14. The membrane assembly according to claim 13, wherein the tension member is U-shaped.

15. The membrane assembly according to claim 13, wherein the tension member is pivotable between the operative position and an inoperative position, where the tension member is pivoted away from the flexible membrane.

16. An apparatus for obtaining a topographical plantar image of a foot, the apparatus comprising:

a three-dimensional imager;

a housing comprising a top wall having an opening formed therethrough, a bottom wall positioned on the three-dimensional imager, the bottom wall being optically transparent on at least a portion thereof, a sidewall interconnecting the top wall and the bottom wall, and a support structure connected to the top wall along a periphery of the opening, the support structure having a front end and a rear end, the rear end being elevated relative to the front end; and a flexible membrane to receive thereon the foot, the flexible membrane being suspended from the support structure and extending across and hermetically sealing the opening, the flexible membrane including a forefoot-receiving region and a rearfoot-receiving region respectively adjacent to the front end and the rear end of the support structure, the rearfoot-receiving region being under less tension than the forefoot-receiving region, the flexible membrane and the housing together defining an inflatable chamber, the flexible membrane being configured, upon inflation of the inflatable chamber, to inflate and to support, alone, an entire plantar surface of the foot in a spaced-apart and contactless relationship with the bottom wall, the three-dimensional imager being configured to acquire the topographical plantar image through the optically transparent portion of the bottom wall.

17. The apparatus according to claim 16, wherein the three-dimensional imager is one of a three-dimensional laser scanner and a three-dimensional digital stereo imaging system.

18. A method for imaging a foot having a front portion and a rear portion, the method comprising:

providing a flexible membrane suspended from a support structure having a front end and a rear end elevated relative to the front end, the flexible membrane defining an upper portion of an inflatable chamber, the flexible membrane including a forefoot-receiving region and a rearfoot-receiving region respectively affixed to the front end and the rear end of the support structure, the rearfoot-receiving region being under less tension than the forefoot-receiving region;

adjusting an internal pressure of the inflatable chamber to inflate the inflatable chamber including the flexible membrane;

positioning the foot on the flexible membrane in a semi-weight-bearing condition with an entire plantar surface of the foot being received on and supported solely by the flexible membrane in a spaced-apart and contactless relationship with a lower portion of the inflatable chamber, the front and rear portions of the foot being respectively located in the forefoot and rearfoot-receiving regions of the membrane; and acquiring a topographical plantar image of the foot positioned on the flexible membrane in the semi-weight-bearing condition.

19. The method according to claim 18, wherein the providing step comprises preforming the flexible membrane with a predetermined shape to provide the rearfoot-receiving region with a concave recessed area.

20. The method according to claim 18, wherein the providing step comprises mounting the flexible membrane to the support structure so that the flexible membrane has a concave recessed area in the rearfoot-receiving region.

21. The method according to claim 18, wherein the providing step comprises securing the flexible membrane to the support structure.

22. The method according to claim 18, further comprising, between the positioning step and the acquiring step, a step of readjusting the internal pressure of the inflatable chamber.

23. The method according to claim 18, further comprising, between the providing step and the adjusting step, a step of applying a compressive load on the flexible membrane along a peripheral portion of the forefoot-receiving region.

24. An apparatus for obtaining a topographical plantar image of a foot, the apparatus comprising:

a housing comprising a top wall having an opening formed therethrough, a bottom wall, a sidewall interconnecting the top wall and the bottom wall, and a support structure connected to the top wall along a periphery of the opening, the support structure having a front end and a rear end, the rear end being elevated relative to the front end;

a three-dimensional imager inside the housing; and a flexible membrane to receive thereon the foot, the flexible membrane suspended from the support structure and extending across and sealing the opening, the flexible membrane including a forefoot-receiving region and a rearfoot-receiving region respectively adjacent to the front end and the rear end of the support structure, the rearfoot-receiving region being under less tension than the forefoot-receiving region, the flexible membrane and the housing together defining an inflatable chamber containing the three-dimensional imager, the flexible membrane being configured, upon inflation of the inflatable chamber, to inflate and to support, alone, an entire plantar surface of the foot in a spaced-apart and contactless relationship with a top surface of the three-dimensional imager, the three-dimensional imager configured to acquire the topographical plantar image from under the flexible membrane.

25. The apparatus according to claim 24, wherein the flexible membrane is preformed with a predetermined shape to provide a concave recessed area in the rearfoot-receiving region.

26. The apparatus according to claim 24, further comprising a tension member connected to the housing and configured, upon inflation of the inflatable chamber, to be in an operative position, where the tension member is urged against and exerts a downwardly directed force on a peripheral portion of the forefoot-receiving region of the flexible membrane.

27. The apparatus according to claim 16, wherein the flexible membrane is preformed with a predetermined shape to provide a concave recessed area in the rearfoot-receiving region.

28. The apparatus according to claim 16, further comprising a tension member connected to the housing and configured, upon inflation of the inflatable chamber, to be in an operative position, where the tension member is urged against and exerts a downwardly directed force on a peripheral portion of the forefoot-receiving region of the flexible membrane.

* * * * *